US008410127B2

(12) United States Patent
Song et al.

(10) Patent No.: US 8,410,127 B2
(45) Date of Patent: Apr. 2, 2013

(54) SUBSTITUTED TETRAZOL-1-YL-PHENOXYMETHYL-THIAZOL-2-YL-PIPERIDINYL-PYRIMIDINE SALTS

(75) Inventors: Jiangao Song, Hayward, CA (US); Charles A. McWherter, Hayward, CA (US); Fang Ma, Hayward, CA (US); Mark Andres, West Lafayette, IN (US); Igor Ivanisevic, West Lafayette, IN (US); Ekaterina Albert, West Lafayette, IN (US); Patricia Andres, West Lafayette, IN (US)

(73) Assignee: Metabolex, Inc., Hayward, CA (US)

( * ) Notice: Subject to any disclaimer, the term of this patent is extended or adjusted under 35 U.S.C. 154(b) by 0 days.

(21) Appl. No.: 12/886,470

(22) Filed: Sep. 20, 2010

(65) Prior Publication Data
US 2011/0152270 A1 Jun. 23, 2011

Related U.S. Application Data

(60) Provisional application No. 61/247,936, filed on Oct. 1, 2009.

(51) Int. Cl.
*A01N 43/54* (2006.01)
*A61K 31/505* (2006.01)

(52) U.S. Cl. .......................................... 514/275; 544/331
(58) Field of Classification Search .................. 544/297
See application file for complete search history.

(56) References Cited

U.S. PATENT DOCUMENTS

| 3,536,809 | A |  | 10/1970 | Applezweig |
|---|---|---|---|---|
| 3,598,123 | A |  | 8/1971 | Zaffaroni |
| 3,778,443 | A |  | 12/1973 | Prakash |
| 3,845,770 | A |  | 11/1974 | Theeuwes et al. |
| 3,916,899 | A |  | 11/1975 | Theeuwes et al. |
| 4,008,719 | A |  | 2/1977 | Theeuwes et al. |
| 4,673,564 | A |  | 6/1987 | Kawata et al. |
| 4,894,235 | A |  | 1/1990 | Kohne et al. |
| 5,013,556 | A |  | 5/1991 | Woodle et al. |
| 5,340,591 | A |  | 8/1994 | Nakano et al. |
| 5,420,298 | A |  | 5/1995 | Edwards et al. |
| 5,456,923 | A |  | 10/1995 | Nakamichi et al. |
| 5,707,646 | A |  | 1/1998 | Yajima et al. |
| 5,817,667 | A |  | 10/1998 | Chu et al. |
| 5,817,677 | A |  | 10/1998 | Linz et al. |
| 5,939,099 | A |  | 8/1999 | Grabowski et al. |
| 6,020,346 | A |  | 2/2000 | Armour et al. |
| 6,051,712 | A |  | 4/2000 | Binggeli et al. |
| 6,221,660 | B1 |  | 4/2001 | Bonini et al. |
| 6,274,735 | B1 |  | 8/2001 | Lohri et al. |
| 6,468,756 | B1 |  | 10/2002 | Bonini et al. |
| 7,108,991 | B2 |  | 9/2006 | Chen et al. |
| 7,638,541 | B2 | * | 12/2009 | Chen et al. .................... 514/365 |
| 8,183,381 | B2 |  | 5/2012 | Ma et al. |
| 8,227,495 | B2 |  | 7/2012 | Chen et al. |
| 2002/0099214 | A1 |  | 7/2002 | Gibson et al. |
| 2002/0198223 | A1 |  | 12/2002 | Allerton et al. |
| 2003/0064990 | A1 |  | 4/2003 | Denton et al. |
| 2004/0024218 | A1 |  | 2/2004 | Barlocco et al. |
| 2005/0165005 | A1 |  | 7/2005 | Genevois-Borella et al. |
| 2006/0135501 | A1 |  | 6/2006 | Knox et al. |
| 2006/0142262 | A1 |  | 6/2006 | Jones et al. |
| 2006/0155128 | A1 |  | 7/2006 | Jones et al. |
| 2009/0054475 | A1 | * | 2/2009 | Chen et al. .................... 514/275 |
| 2009/0137590 | A1 |  | 5/2009 | Ma et al. |
| 2009/0270404 | A1 | * | 10/2009 | Wilson et al. ................. 514/249 |
| 2009/0286812 | A1 |  | 11/2009 | Erickson et al. |
| 2010/0087465 | A1 | * | 4/2010 | Chen et al. .................... 514/275 |
| 2010/0130511 | A1 | * | 5/2010 | Chen et al. .................... 514/256 |
| 2011/0137032 | A1 |  | 6/2011 | Endo et al. |
| 2011/0160222 | A1 |  | 6/2011 | Chen et al. |
| 2011/0263617 | A1 | * | 10/2011 | Mark et al. ................. 514/262.1 |
| 2011/0294836 | A1 |  | 12/2011 | Song et al. |
| 2011/0313160 | A1 | * | 12/2011 | Chen et al. .................... 544/331 |
| 2011/0318418 | A1 | * | 12/2011 | McWherter et al. .......... 424/489 |
| 2012/0184572 | A1 |  | 7/2012 | Song et al. |

FOREIGN PATENT DOCUMENTS

| CL | 27752002 | 6/2001 |
|---|---|---|
| CL | 28992000 | 7/2001 |
| CL | 21302008 | 1/2009 |
| CL | 21312008 | 1/2009 |
| CL | 20932008 | 5/2009 |
| CL | 21382008 | 10/2009 |
| CL | 21392008 | 10/2009 |
| DE | 2 701 705 A1 | 8/1977 |
| EP | 0 630 887 A1 | 12/1994 |
| EP | 0 755 923 | 1/1997 |
| EP | 0 755 923 A1 | 1/1997 |
| EP | 0 867 183 | 9/1998 |
| EP | 0 867 183 A1 | 9/1998 |
| EP | 0 901 786 | 3/1999 |
| EP | 1 092 727 A2 | 4/2001 |
| EP | 1 129 706 A2 | 9/2001 |
| EP | 1 176 147 A1 | 1/2002 |
| EP | 1 422 228 A1 | 5/2004 |
| EP | 1 500 648 A1 | 1/2005 |
| EP | 1 133 559 B1 | 8/2005 |
| EP | 1 584 683 B1 | 7/2007 |

(Continued)

OTHER PUBLICATIONS

S.L. Morissette et al., Advanced Drug Delivery Reviews, 56, 275-300 (2004).* S.R. Vippagunta et al., Advanced Drug Delivery Reviews, 48, 3-26 (2001).*
J.K. Guillory, Generation of Polymorphs, Hydrates, Solvates, and Amorphous Solids, in Polymorphism in Pharmaceutical Solids 183-220 (H.G. Brittain ed., 1999).*
L.D. Bighley et al., Salt Forms and Absorption, in 13 Encyclopedia of Pharmaceutical Technology 453 (M Swarbrick and J. Boylan eds., 1996).*
U.S. Appl. No. 13/006,298, filed Jan. 13, 2011, Song et al.
U.S. Appl. No. 13/032,513, filed Feb. 22, 2011, Chen et al.

(Continued)

*Primary Examiner* — James O Wilson
*Assistant Examiner* — Alexander R Pagano
(74) *Attorney, Agent, or Firm* — Foley & Lardner LLP

(57) ABSTRACT

Crystalline salts of 5-ethyl-2-{4-[4-(4-tetrazol-1-yl-phenoxymethyl)-thiazol-2-yl]-piperidin-1-yl}-pyrimidine, compositions thereof, methods for their preparation, and methods for their use are disclosed.

12 Claims, 23 Drawing Sheets

FOREIGN PATENT DOCUMENTS

| | | |
|---|---|---|
| EP | 1 813 606 A1 | 8/2007 |
| EP | 1 852 433 | 11/2007 |
| GB | 0 882 813 | 11/1961 |
| GB | 1 422 263 A | 1/1976 |
| WO | WO-00/50562 A2 | 8/2000 |
| WO | WO-02/098223 A1 | 5/2002 |
| WO | WO-2004/037809 A1 | 5/2004 |
| WO | WO-2004/078413 A1 | 9/2004 |
| WO | WO-2004/089373 A1 | 10/2004 |
| WO | WO-2004/113323 A1 | 12/2004 |
| WO | WO-2005/011654 A2 | 2/2005 |
| WO | WO-2005/061489 A1 | 7/2005 |
| WO | WO-2005/061547 A2 | 7/2005 |
| WO | WO-2005/082089 | 9/2005 |
| WO | WO-2005/121088 A1 | 12/2005 |
| WO | WO-2006/054652 A1 | 5/2006 |
| WO | WO-2006/074057 | 7/2006 |
| WO | WO-2006/076231 A2 | 7/2006 |
| WO | WO-2006/091428 A2 | 8/2006 |
| WO | WO-2006/124692 A2 | 11/2006 |
| WO | WO-2006/133216 A2 | 12/2006 |
| WO | WO-2006/134487 A1 | 12/2006 |
| WO | WO-2007/003960 A1 | 1/2007 |
| WO | WO-2007/003961 A2 | 1/2007 |
| WO | WO-2007/023507 A2 | 3/2007 |
| WO | WO-2007/035355 A2 | 3/2007 |
| WO | WO-2007/039177 A2 | 4/2007 |
| WO | WO-2007/120702 A2 | 10/2007 |
| WO | WO-2008/008887 A2 | 1/2008 |
| WO | WO-2008/025800 | 3/2008 |
| WO | WO-2008/070692 | 6/2008 |
| WO | WO 2008/083238 A2 | 7/2008 |
| WO | WO 2008083238 A2 * | 7/2008 |
| WO | WO-2008/109702 A1 | 9/2008 |
| WO | WO-2008/137436 | 11/2008 |
| WO | WO-2009/010429 | 1/2009 |
| WO | WO-2009/010761 | 1/2009 |
| WO | WO-2009/014637 | 1/2009 |
| WO | WO-2009/016516 | 2/2009 |
| WO | WO-2009/037394 | 3/2009 |
| WO | WO-2009/070869 A1 | 6/2009 |
| WO | WO-2010/008739 A2 | 1/2010 |
| WO | WO-2010/013849 A1 | 2/2010 |
| WO | WO-2010/029089 | 3/2010 |
| WO | WO-2010/048149 A2 | 4/2010 |
| WO | WO-2011/041154 | 4/2011 |

OTHER PUBLICATIONS

U.S. Appl. No. 13/152,752, filed Jun. 3, 2011, Chen et al.
U.S. Appl. No. 13/165,651, filed Jun. 21, 2011, McWherter et al.
"Report of the Expert Committee on the Diagnosis and Classification of Diabetes Mellitus", Diabetes Care, (2003) vol. 26 (Suppl 1): S5-19.
Ashcroft et al., "ATP-sensitive K+ channels and insulin secretion: their role in health and disease." Diabetologia (1999) 42: 903-919.
Barrett-Conner, "Epidemiology, obesity, and non-insulin-dependent diabetes mellitus." Epidemol Rev (1989) 11: 172-181.
Bell et al., "Diabetes mellitus and genetically programmed defects in ?-cell function." Nature (2001) 414: 788-791.
Blicklé, "Meglitinide analogues: a review of clinical data focused on recent trials." Diabetes Metab (2006) 32(2): 113-120.
Brubaker, "The Glucagon-Like Peptides Pleiotropic Regulators of Nutrient Homeostatsis." Ann N Y Acad Sci (2006) 1070: 10-26.
Cantin et al., "PDE-10A inhibitors as insulin secretagogues." Bioorg Med Chem Lett (2007) 17(10): 2869-2873).
Castro et al. "Enhancement of Oral Absorption in Selective 5-HT1D Receptor Agonists: Fluorinated 3[3-(Piperidin-1-yl)propyl]indoles." J. Med. Chem. (1998) 41: 2667-2670.
Cavaghan et al., "Interactions between insulin resistance and insulin secretion in the development of glucose intolerance." J Clin Invest (2000) 106(3): 329-333.
Chiasson et al., "The Efficacy of Acarbose in the Treatment of Patients with Non-Insulin-dependent Diabetes Mellitus: A Multicenter Controlled Clinical Trial." Ann Intern Med (1994) 121(12): 928-935.

Choi et al., "Alterations in regulation of energy homeostasis in cyclic nucleotide phosphodiesterase 3B-null mice." J Clin Invest (2006) 116(12): 3240-3251.
Coniff et al., "Acarbose: A Review of US Clinical Experience." Clin Ther (1997) 19(1): 16-26.
Coniff et al., "Multicenter, Placebo-Controlled Trial Comparing Acarbose (BAY g 5421) With Placebo, Tolbutamide, and Tolbutamide-Plus-Acarbose in Non-Insulin-Dependent Diabetes Mellitus." Am J Med (1995) 98: 443-451.
Deacon. "Dipeptidyl peptidase 4 inhibition with sitagliptin: a new therapy for Type 2 diabetes." Expert Opinion on Investigational Drugs (2007) 16(4):533-545.
Deng et al. "A novel and efficient synthesis of 2,5-substituted 1,2,4-triazol-3-ones" Tetrahedron Letters, vol. 46, No. 46, 2005, pp. 7993-7996, XP005113190.
Drucker, "The role of gut hormones in glucose homeostasis." J Clin Invest (2007) 117(1): 24-32.
Elahi et al., "The insulinotropic actions of glucose-dependent insulinotropic polypeptide (GIP) and glucagon-like peptide-1 (7-37) in normal and diabetic subjects." Regul Pept (1994) 51: 63-74.
Farilla et al., "Glucagon-Like Peptide 1 Inhibits Cell Apoptosis and Improves glucose Responsiveness of Freshly Isolated Human Islets." Endocrinology (2003) 144(12): 5149-5158.
Farilla et al., "Glucagon-Like Peptide-1 Promotes Islet Cell Growth and Inhibits Apoptosis in Zucker Diabetic Rats." Endocrinology (2002) 143(11): 4397-4408.
Filipsson et al., "The Neuropeptide Pituitary Adenylate Cyclase-Activating Polypeptide and Islet Function." Diabetes (2001) 50(9): 1959-1969.
Flier, "Insulin Receptors and Insulin Resistance." Ann Rev Med (1983) 34: 145-160.
Friedrichsen et al., "Stimulation of pancreatic β-cell replication by incretins involves transcriptional induction of cyclin D1 via multiple signalling pathways." J Endocrinol (2006) 188(3): 481-492.
Furman et al., "Modulation of cyclic nucleotides and cyclic nucleotide phosphodiesterases in pancreatic islet β-cells and intestinal L-cells as targets for treating diabetes mellitus." Curr Opin Investig Drugs (2006) 7(10): 898-905.
Gilon et al., "Mechanisms and Physiological Significance of the Cholinergic Control of Pancreatic β-Cell Function." Endocr Rev (2001) 22(5): 565-604.
Gloyn et al., "Insights into the Structure and Regulation of Glucokinase from a Novel Mutation (V62M), Which Causes Maturity-onset Diabetes of the Young." J Biol Chem (2005) 280(14): 14105-14113.
González et al., "Investigational treatments for type 2 diabetes mellitus: exenatide and liraglutide." Expert Opin Investig Drugs (2006) 15(8): 887-895.
Green et al. "Dipeptidyl peptidase IV (DPP IV) inhibitors: a newly emerging drug class for the treatment of type 2 diabetes." Diabetes Vasc. Dis. Res. (2006), 3:159-165.
Gromada et al., "Glucagon-Like Peptide 1(7-36) Amide Stimulates Exocytosis in Human Pancreatic beta-Cells by Both Proximal and Distal Regulatory Steps in Stimulus-Secretion Coupling." Diabetes (1998) 47(1): 57-65.
Guertin et al., "Small Molecule Glucokinase Activators as Glucose Lowering Agents: A New Paradigm for Diabetes Therapy." Curr Med Chem (2006) 13(15): 1839-1843.
Haffner, "Management of Dyslipidemia in Adults With Diabetes." Diabetes Care (1998) 21(1): 160-178.
Han et al., "The Calcium/Calmodulin-dependent Phosphodiesterase PDE1C Down-regulates Glucose-induced Insulin Secretion." J Biol Chem (1999) 274(32): 22337-22344.
Hansen, "Towards Selective Kir6.2/SUR1 Potassium Channel Openers, Medicinal Chemistry and Therapeutic Perspectives." Curr Med Chem (2006) 13(4): 361-376.
Hansotia et al., "Extrapancreatic incretin receptors modulate glucose homeostasis, body weight, and energy expenditure." J Clin Invest (2007) 117(1): 143-152, Epub Dec. 21, 2006.
Härndahl et al., "Important Role of Phosphodiesterase 3B for the Stimulatory Action of cAMP on Pancreatic β-Cell Exocytosis and Release of Insulin." J Biol Chem (2002) 277(40): 37446-37455.

Hatakeyama et al., "Rapid glucose sensing by protein kinase A for insulin exocytosis in mouse pancreatic islets." J Physiol (2006) 570(Pt 2): 271-282.

Henquin, "Pathways in β-Cell Stiumulus-Secretion Coupling as Taragets fro Therepeutic Insulin Secretagogues." Diabetes (2004) 53, Suppl. 3, S48-S58.

Holz, "Perspectives in Diabetes Epac: A New cAMP-Binding Protein in Support of Glucagon-Like Peptide-1 Receptor-Mediated Signal Transduction in the Pancreatic β-Cell." Diabetes (2004) 53(1): 5-13.

Hussain et al., "Increased Pancreatic β-Cell Proliferation Mediated by CREB Binding Protein Gene Activation." Mol Cell Biol (2006) 26(20): 7747-7759.

Iwamoto et al., "Effect of Combination Therapy of Troglitazone and Sulphonylureas in Patients with Type 2 Diabetes Who Were Poorly Controlled by Sulphonylurea Therapy Alone." Diabet Med (1996) 13: 365-370.

Kahn, "The Importance of β-Cell Failure in the Development and Progression of Type 2 Diabetes." J Clin Endicrinol Metab (2001) 86:4047-4058.

Kahn, "The Importance of the β-Cell in the Pathogenesis of Type 2 Diabetes Mellitus." Am J Med (2000) 108 Suppl 6a, 2S-8S.

Kahn, "Type 2 Diabetes: When Insulin Secretion Fails to Compensate for Insulin Resistance." Cell (1998) 92: 593-596.

Kaplan et al., "Cardiovascular diseases" in Health and Human Behavior, pp. 206-242 (McGraw-Hill, New York 1993).

Kashima et al., "Critical Role of cAMP-GEFII Rim2 Complex in Incretin-potentiated Insulin Secretion." J Biol Chem (2001) 276(49): 46046-46053, Epub Oct. 11, 2001.

Kim et al., "(2R)-4-oxo-4-[3-(triflouromethyl)-5,6-dihydro[1,2,4]triazolo[4,3-a]pyrazin-7(8H)-yl]-1-(2,4,5-triflourophenyl)butan-2-amine: a potent, orally active dipeptidyl peptidase IV inhibitor for the treatment of type 2 diabetes." J Med Chem. 48(1):141-151. 2005.

Kim et al., "Exendin-4 induction of cyclin D1 expression in INS-1 β-cells: involvement of cAMP-responsive element." J Endocrinol (2006) 188(3): 623-633.

Knowler et al., "Obesity in the Pima Indians: its magnitude and relationship with diabetes1,2." Am J Clin Nutr (1991) 53: 1543S-1551S.

Kwiterovich, "State-of-the-Art Update and Review: Clinical Trials of Lipid-Lowering Agents." Am J Cardiol (1998) 82(12A): 3U-17U.

Langer, "New Methods of Drug Delivery." Science (1990) 249: 1527-1533.

Levy et al., "Beta-cell Deterioration Determines the Onset and Rate of Progression of Secondary Dietary Failure in Type 2 Diabetes Mellitus: the 10-year Follow-up of the Belfast Diet Study." Diabetes Med (1998) 15: 290-296.

Li et al., "Glucagon-like Peptide-1 Receptor Signaling Modulates β Cell Apoptosis." J Biol Chem (2003) 278(1): 471-478.

Mahler et al., "Clinical Review 102 Type 2 Diabetes Mellitus: Update on Diagnosis, Pathophysiology, and Treatment." J Clin Endocrinol Metab (1999) 84(4): 1165-1171.

Matschinsky et al., "Perspectives in Diabetes the Network of Glucokinase-Expressing Cells in Glucose Homeostasis and the Potential of Glucokinase Activators for Diabetes Therapy." Diabetes (2006) 55(1): 1-12.

Matschinsky, "Glucokinase, Glucose Homeostasis, and Diabetes Mellitus." Curr Diab Rep (2005) 5(3): 171-176.

Meneilly et al., "The Effect of Glyburide on β-Cell Sensitivity to Glucose-Dependent Insulinotropic Polypeptide." Diabetes Care (1993) 16(1): 110-114.

Miura et al., "Glucagon-like peptide-1 induces a cAMP-dependent increase of [Na+]i associated with insulin secretion in pancreatic β-cells." Am J Physiol Endocrinol Metab (2003) 285, E1001-E1009.

Nauck et al., "Preserved Incretin Activity of Glucagon-like Peptide 1 [7-36 Amide] but Not of Synthetic Human Gastric Inhibitory Polypeptide in Patients with type-2 Diabetes Mellitus." J Clin Invest (1993) 91: 301-307.

Prentki et al., "Islet β cell Failure in type 2 dieabetes." J Clin Invest (2006) 116(7): 1802-1812.

Qader et al., "Expression of islet inducible nitric oxide synthase and inhibition of glucose-stimulated insulin release after long-term lipid infusion in the rat is counteracted by PACAP27." Am J Physiol Endocrinol Metab (2007) 292(5): E1447-E1455.

Reaven, "Insulin Resistance and Human Disease: A Short History." J Basic & Clin Phys & Pharm (1998) 9: 387-406.

Reimann et al., "Signaling Mechanisms Underlying the Release of Glucagon-Like Peptide 1." Diabetes (2006) 55(Suppl 2): S78-S85.

Rendell, "The Role of Sulphonylureas in the Management of Type 2 Diabetes Mellitus." Drugs (2004) 64(12): 1339-13.58.

Saltiel, "New Perspectives into the Molecular Pathogenesis and Treatment of Type 2 Diabetes." Cell (2001) 104: 517-529.

Saxena et al., "Genome-Wide Association Analysis Identifies Loci for Type 2 Diabetes and Triglyceride Levels." Science (2007) 316: 1331-1336.

Seino, "ATP-Sensitive Potassium Channels: A Model of Heteromultimeric Potassium Channel/Receptor Assemblies." Annu Rev Physiol (1999) 61: 337-362.

Shibasaki et al., "Interaction of ATP Sensor, cAMP Sensor, Ca2+ Sensor, and Voltage-dependent Ca2+ Channel in Insulin Granule Exocytosis." J Biol Chem (2004) 279(9): 7956-7961.

Soga et al., "Lysophosphatidylcholine enhances glucose-dependent insulin secretion via an orphan G-protein-coupled receptor." Biochem. Biophys Res Commun., Jan. 28, 2005, vol. 326, No. 4, pp. 744-751.

Steinthorsdottir et al., "A variant in CDKAL1 influences insulin response and risk of type 2 diabetes." Nature Genetics (2007) 39(6): 770-775.

Still et al., "Rapid Chromatographic Technique for Preparative Separations with Moderate Resolution." J. Org. Chem. 1978, 43 (14), 2923-5.

Thorens et al., "Cloning and Functional Expression of the Human Islet GLP-1 Receptor: Demonstration that Exendin-4 is an Agonist and Exendin-(9-39) an Antagonist of the Receptor." Diabetes (1993) 42, 1678-1682.

Thorens, "GLUT2 in pancreatic and extra-pancreatic gluco-detection." Mol Membr Biol (2001) 18(4): 265-273.

Turner et al., "Glycemic Control With Diet, Sulfonylurea, Metformin, or Insulin in Patients With Type 2 Diabetes Mellitus: Progressive Requirement for Multiple Therapies (UKPDS 49)." JAMA (1999) 281(21): 2005-2012.

Turner et al., "Insulin resistance, impaired glucose tolerance and non-insulin-dependent diabetes, pathologic mechanisms and treatment: Current status and therapeutic possibilities." Prog Drug Res (1998) 51: 33-94.

United Kingdom Prospective Diabetes Study Group: "UKPDS 28: A Randomized Trial of Efficacy of Early Addition of Metformin in Sulfonylurea-Treated Type 2 Diabetes." Diabetes Care (1998) 21(1): 87-92.

Vilsbøll et al., "Reduced Postprandial Concentrations of Intact Biologically Active Glucagon-Like Peptide 1 in Type 2 Diabetic Patients." Diabetes (2001) 50: 609-613.

Walz et al., "Early and rapid development of insulin resistance, islet dysfunction and glucose intolerance after high-fat feeding in mice overexpressing phosphodiesterase 3B." J Endocrinol (2006) 189(3): 629-641.

Yamada et al., "Cytosolic Ca2+ responses to sub-picomolar and nanomolar PACAP in pancreatic β-cells are mediated by VPAC2 and PAC1 receptors." Regul Pept (2004) 123(1-3): 147-153.

Zhou et al., "Overexpression of Repressive cAMP Response Element Modulators in High Glucose and Fatty Acid-treated Rat Islets." J Biol Chem (2003) 278(51): 51316-51323.

U.S. Appl. No. 13/449,238, filed Apr. 17, 2012, Xin et al.
U.S. Appl. No. 13/463,617, filed May 3, 2012, Jingyuan et al.
U.S. Appl. No. 13/612,451, filed Sep. 12, 2012, Xin et al.

Annoura, et al., "Synthesis and Biological Evaluation of New 4-Arlypiperidines and 4-Aryl-4-piperidinols: Dual Na+ and Ca2+ Channel Blockers with Reduced Affinity for Dopamine D2 Receptors," Biorganic & Medicinal Chemistry, (2002), 10:371-383.

Blough, et al., "Synthesis and Transporter Binding Properties of 3.beta.-[4'(Phenylalkyl,—phenylalkenyl, anda -phenylalkynl)phenyl]tropane-2.beta.-carboxylic Acid Methyl Esters: Evidence of a Remote Phenyl Binding Domain on the Dopamine Transporter," J. Medicinal Chemistry, (2002), 45(18):4029-4037.

Byrn et al., "Solid-State Chemistry of Drugs, 11: Hydrates and Solvates" 2nd ed., 1999: 233-247, 516.

Cavalla. et al., "Analgetics Based on the Pyrrolidine Ring. V," J. of Medicinal Chemistry, (1970), 13(5):794-800.

Gould, W.A., et al., "Pyrrolidines. IX. 3-Aryl-3-pyrrolidinols," J. Medicinal Chemistry, (1964), 7(1):60-67.

Le Bourdonnec, et al., "Synthesis and structure-activity relationships of a new series of 2alpha-substitued trans-4,5-dimethyl-4-(3-hydroxyphenyl)piperidine as mu-selective opioid antagonists," Bioorganic and Medicinal Chemistry Letters, (2006), 16(4):864-868.

Sato, et al., "New mu-Opioid Receptor Agonists with Phenoxyacetic Acid Moiety," Chem. Pharm. Bull., (2002), 50(2):292-297.

Singer et al., "Synthesis of SAR of tolylamine 5-HT6 antagonists," Bioorganic & Medicinal Chemistry Letters 19 (2009): 2409-2412.

Thomas, et al., "Investigation of the N-Substituent Conformation Governing Potency and.mu. Receptor Subtype-Selectivity in ( )-(3R,4R)-Dimethyl-4-(3-hydroxyphenyl)-piperidine Opioid Antagonists," J. Medicinal Chemistry, (1998), 41(11):1980-1990.

Waid, et al., "Constrained Amino Acids, An Approach to the Synthesis of 3-Substituted Prolines," Tetrahedron Letters, (1996), 37(24):4091-4094.

Wu, et al., "Pyrrolidines. VII. 3-Hydroxy-1-Pyrrolidinecarboxylic Acid Esters," J. Medicinal Chemistry, (1962), 5(4):752-762.

International Search Report and Written Opinion dated Feb. 22, 2010 in related PCT Application No. PCT/US2009/047551.

International Search Report and Written Opinion dated Jan. 26, 2009 in related PCT Application No. PCT/US2008/069714.

International Search Report and Written Opinion dated Jun. 19, 2009 in related PCT Application No. PCT/US2009/038847.

International Search Report and Written Opinion dated May 23, 2008 in related PCT Application No. PCT/US2007/088978.

International Search Report and Written Opinion dated Oct. 29, 2010 in related PCT Application No. PCT/US2010/049486.

International Search Report dated Oct. 10, 2011 in related PCT Application No. PCT/US2011/040972.

International Search Report dated Oct. 6, 2011 in related PCT Application No. PCT/US11/39069.

Supplementary European Search Report dated Mar. 4, 2011 in related European Application No. 07869989.9.

Supplementary Partial European Search Report dated Jul. 25, 2012 in related European Application No. 09798422.3.

Annoura et al., "Synthesis and Biological Evaluation of New 4-Arylpiperidines and 4-Aryl-4-piperidinols: Dual $Na^+$ and $Ca^{2+}$ Channel Blockers with Reduced Affinity for Dopamine $D_2$ Receptors", Bioorganic and Medicinal Chemistry, 2002, 10:371-383.

Blough et al., "Synthesis and Transporter Binding Properties of 3β-[4'-Phenylalkyl, -phenylalkenyl, and —phenylalkynl)phenyl]tropane-2β-carboxylic Acid Methyl Esters: Evidence of a Remote Phenyl Binding Domain on the Dopamine Transporter", Journal of Medicinal Chemistry, 2002, 45(18):4029-4037.

Crawley et al., Methoxytetrahydropryrans. A New Series of Selective and Orally Potent 5-Lipoxygenase Inhibitor, Journal of Medicinal Chemistry, 1992, 35(14):2600-2609.

Deng et al., "A novel and efficient synthesis of 2,5-substituted 1,2,4-triazol-3-ones" Tetrahedron Letters, 2005, 46(46):7993-7996.

Gould, "Salt selection for basic drugs," Int. J. Pharma., 1986, 33:201-217.

Greene, "Protective Groups in Organic Synthesis," 1999, 518-523.

Le Bourdonnec et al., "Synthesis and structure-activity relationships of a new series of 2α- substituted *trans*-4,5-dimethyl-4-(3-hydroxyphenyl)piperidine as μ-selective opioid antagonists", Bioorganic & Medicinal Chemistry Letters, 2006, 16(4):864-868.

Thomas et al., "Investigation of the N-Substituent Conformation Governing Potency and μ Receptor Subtype-Selectivity in (+)-(3R,4R)-Dimethyl-4-(3-hydroxyphenyl)-piperidine Opioid Antagonists", Journal of Medicinal Chemistry, 1998, 41(11):1980-1990.

* cited by examiner

SUBSTITUTED TETRAZOL-1-YL-PHENOXYMETHYL-THIAZOL-2-YL-PIPERIDINYL-PYRIMIDINE SALTS

FIELD OF THE INVENTION

Provided are crystalline salts of 5-ethyl-2-{4-[4-(4-tetrazol-1-yl-phenoxymethyl)-thiazol-2-yl]-piperidin-1-yl}-pyrimidine, compositions thereof, methods for their preparation, and methods for their use.

BACKGROUND OF THE INVENTION

WO 2008/083238 discloses 5-ethyl-2-{4-[4-(4-tetrazol-1-yl-phenoxymethyl)-thiazol-2-yl]piperidin-1-yl}-pyrimidine and its uses for the treatment of diabetes and metabolic disorders. PCT/US2009/038847 discloses uses of oxymethylene compounds including 5-ethyl-2-{4-[4-(4-tetrazol-1-yl-phenoxymethyl)-thiazol-2-yl]-piperidin-1-yl}-pyrimidine in a combination therapy with a dipeptidyl peptidase IV (DPP IV) inhibitor. A need exists for improved therapies for the treatment of diseases relating to diabetes and metabolic disorders.

BRIEF SUMMARY OF THE INVENTION

In one embodiment, the present invention provides crystalline salts of 5-ethyl-2-{4-[4-(4-tetrazol-1-yl-phenoxymethyl)-thiazol-2-yl]-piperidin-1-yl}-pyrimidine selected from the group consisting of a besylate, camsylate, esylate, HBr, HCl, mesylate, sulfate, and tosylate salt.

In another embodiment, provided are polymorphs (Form 1 and Form 2) of 5-ethyl-2-{4-[4-(4-tetrazol-1-yl-phenoxymethyl)-thiazol-2-yl]-piperidin-1-yl}-pyrimidine hydrochloride.

In other embodiments, provided are methods for the preparation of a crystalline salt or polymorph described herein.

In other embodiments, provided are compositions comprising a crystalline salt or polymorph described herein and a pharmaceutically acceptable carrier.

In other embodiments, provided are methods for use of a crystalline salt or polymorph described herein to treat a disease selected from the group consisting of Type I diabetes, Type II diabetes and metabolic syndrome, and their uses in the preparation of such medicaments.

In other embodiments, provided are methods for use of a crystalline salt or polymorph described herein for one or more of stimulating insulin production, stimulating glucose-dependent insulin secretion, lowering blood glucose, or lowering blood triglyceride levels, and their uses in the preparation of such medicaments.

In other embodiments, provided are methods for use of a crystalline salt or polymorph described herein in a combination therapy with a therapeutically effective amount of a DPP IV inhibitor.

These and other aspects of the invention are further described in the text that follows.

DETAILED DESCRIPTION OF THE INVENTION

Figure 1:
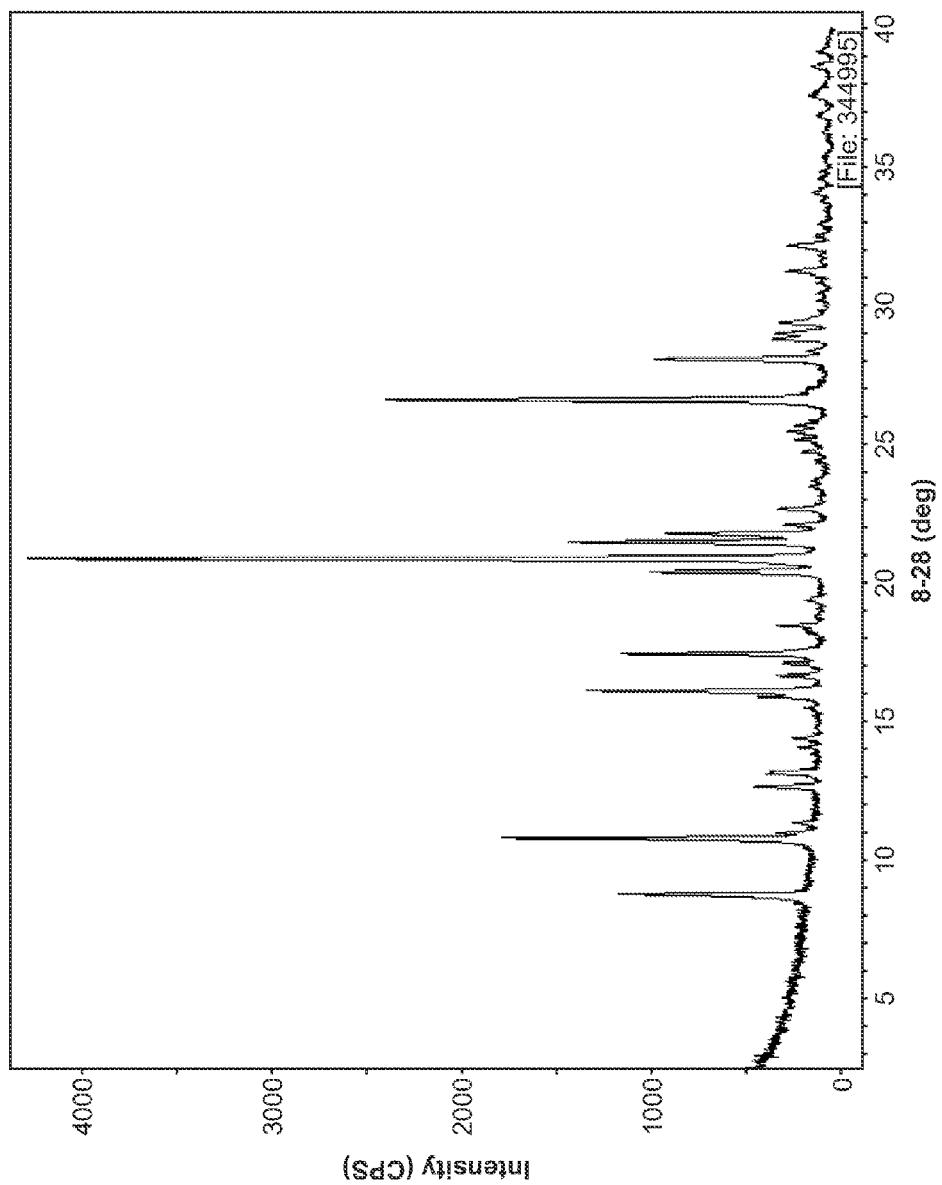
FIG. 1 shows the X-ray powder pattern of HCl salt Form I.

In this specification and in the claims that follow, reference will be made to a number of terms that shall be defined to have the following meanings unless specified otherwise.

Abbreviations

XRPD (x-ray powder diffraction); DSC (differential scanning calorimetry); TGA (thermographic analysis); besylate (benzene sulfonate salt); camsylate (camphorsulfonate salt); esylate (ethanesulfonate salt); mesylate (methanesulfonate salt); tosylate (p-toluene sulfonate salt); acetone ($(CH_3)_2CO$); RH (relative humidity).

As used in the specification and claims, the singular form "a", "an" and "the" include plural references unless the context clearly dictates otherwise.

As used herein, the term "comprising" is intended to mean that the compositions and methods include the recited elements, but not excluding others.

As used herein, the term "about" when used in association with a measurement, or used to modify a value, a unit, a constant, or a range of values, refers to variations of +/−3%.

As used herein, the term "crystalline salt" encompasses anhydrous and unsolvated crystals, as well as crystals that may be associated with varying degrees of hydrates or solvates.

As used herein, the term "substantially" refers to degree of variations of +/− by about 1%, about 5%, about 10%, about 15% or about 20%.

As used herein, the term "substantially pure" with respect to a particular polymorphic form of a compound, means that the polymorph form contains about less than 30%, or about less than 20%, or about less than 15%, or about less than 10%, or about less than 5%, or about less than 1% by weight of impurities, such impurities may include other polymorphic forms of the same compound or trace solvents.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (See, for example, Remington's Pharmaceutical Sciences, 18th Ed. Mack Printing Company, 1990, pp. 1289-1329, incorporated herein by reference.). Except insofar as any conventional carrier is incompatible with the active ingredient, its use in the therapeutic or pharmaceutical compositions is contemplated.

As used herein, the term "subject" refers to a mammal and includes, without limitation, humans, domestic animals (e.g., dogs or cats), farm animals (cows, horses, or pigs), and laboratory animals (mice, rats, hamsters, guinea pigs, pigs, rabbits, dogs, or monkeys).

The term "therapeutically effective amount" refers to that amount of an active ingredient that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by a prescribing physician.

The term "treatment" or "treating" means any treatment of a disease in a mammal, including: (i) preventing the disease, that is, causing the clinical symptoms of the disease not to develop; (ii) inhibiting the disease, that is, arresting the development of clinical symptoms; and/or (iii) relieving the disease, that is, causing the regression of clinical symptoms.

The term "diabetes mellitus" or "diabetes" means a disease or condition that is generally characterized by metabolic defects in production and utilization of glucose that result in the failure to maintain appropriate blood sugar levels in the body. The result of these defects is elevated blood glucose, referred to as "hyperglycemia." Two major forms of diabetes are Type I diabetes and Type II diabetes. As described above, Type I diabetes is generally the result of an absolute deficiency of insulin, the hormone that regulates glucose utilization. Type II diabetes often occurs in the face of normal, or even elevated levels of insulin and can result from the inability of tissues to respond appropriately to insulin. Most Type II diabetic subjects are insulin resistant and have a relative deficiency of insulin, in that insulin secretion cannot compensate for the resistance of peripheral tissues to respond to insulin. In addition, many Type II diabetics are obese. Other types of disorders of glucose homeostasis include impaired glucose tolerance, which is a metabolic stage intermediate between normal glucose homeostasis and diabetes, and gestational diabetes mellitus, which is glucose intolerance in pregnancy in women with no previous history of Type I or Type II diabetes.

The term "metabolic syndrome" refers to a cluster of metabolic abnormalities including abdominal obesity, insulin resistance, glucose intolerance, diabetes, hypertension, hyperlipidemia, and dyslipidemia. These abnormalities are known to be associated with an increased risk of vascular events.

The term "abdominal obesity" is defined by a cutoff point of waist circumference $\geq 102$ cm in men and $\geq 80$ cm in women, as recommended by the third report of the national cholesterol education program expert panel on detection, evaluation, and treatment of high blood cholesterol in adults (NCEP/ATP Panel III).

The term "insulin resistance" can be defined generally as a disorder of glucose metabolism. More specifically, insulin resistance can be defined as the diminished ability of insulin to exert its biological action across a broad range of concentrations producing less than the expected biologic effect (see, e.g., Reaven G M, *J. Basic & Clin. Phys. & Pharm.* (1998) 9:387-406 and Flie J, *Ann Rev. Med.* (1983) 34:145-60). Insulin resistant persons have a diminished ability to properly metabolize glucose and respond poorly, if at all, to insulin therapy.

Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, impaired glucose tolerance, gestational diabetes, metabolic syndrome, hypertension, obesity, atherosclerosis and a variety of other disorders. Eventually, the insulin resistant individuals can progress to a point where a diabetic state is reached.

The term "atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "symptom" of diabetes, includes, but is not limited to, polyuria, polydipsia, and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, e.g., increased susceptibility to certain infections (especially fungal and staphylococcal infections), nausea, and ketoacidosis (enhanced production of ketone bodies in the blood).

The term "complication" of diabetes includes, but is not limited to, microvascular complications and macrovascular complications. Microvascular complications are those complications that generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications that generally result from large blood vessel damage. These complications include, e.g., cardiovascular disease and peripheral vascular disease. Cardiovascular disease refers to diseases of blood vessels of the heart. See, e.g., Kaplan R M, et al., "Cardiovascular diseases" in *Health and Human Behavior*, pp. 206-242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "dyslipidemia" refers to abnormal levels of lipoproteins in blood plasma including both depressed and/or elevated levels of lipoproteins (e.g., elevated levels of LDL and/or VLDL, and depressed levels of HDL).

The term "hyperlipidemia" includes, but is not limited to, the following:

(2) Familial Hyperchylomicronemia, a rare genetic disorder that causes a deficiency in an enzyme, LP lipase, that breaks down fat molecules. The LP lipase deficiency can cause the accumulation of large quantities of fat or lipoproteins in the blood;

(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidemia, also known as multiple lipoprotein-type hyperlipidemia is an inherited disorder where subjects and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine, which can cause reduced affinity of LDL particles for the LDL receptor. Consequently, this can cause high plasma LDL and total cholesterol levels;

(5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated TG levels (and usually not cholesterol levels) and can often be associated with low plasma HDL levels.

Risk factors for hyperlipidemia include, but are not limited to, the following: (1) disease risk factors, such as a history of Type I diabetes, Type II diabetes, Cushing's syndrome, hypothyroidism and certain types of renal failure; (2) drug risk factors, which include, birth control pills; hormones, such as estrogen, and corticosteroids; certain diuretics; and various β blockers; (3) dietary risk factors include dietary fat intake per total calories greater than 40%; saturated fat intake per total calories greater than 10%; cholesterol intake greater than 300 mg per day; habitual and excessive alcohol use; and obesity.

The terms "obese" and "obesity" refers to, according to the World Health Organization, a Body Mass Index ("BMI") greater than 27.8 kg/m² for men and 27.3 kg/m² for women (BMI equals weight (kg)/height (m²). Obesity is linked to a variety of medical conditions including diabetes and hyperlipidemia. Obesity is also a known risk factor for the development of Type II diabetes (see, e.g., Barrett-Conner E, *Epidemol. Rev.* (1989) 11:172-181; and Knowler, et al., *Am. J. Clin. Nutr.* (1991) 53:1543-1551).

The free base 5-ethyl-2-{4-[4-(4-tetrazol-1-yl-phenoxymethyl)-thiazol-2-yl]-piperidin-1-yl}-pyrimidine, MBX-2982, has the structure:

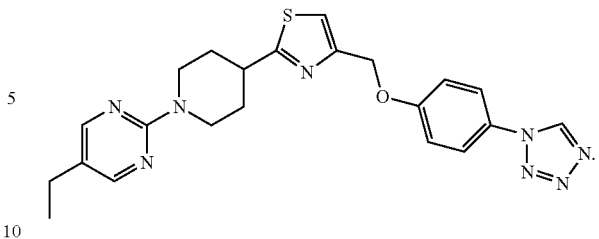

The besylate, camsylate, esylate, HBr, HCl, mesylate, sulfate, and tosylate salts of 5-ethyl-2-{4-[4-(4-tetrazol-1-yl-phenoxymethyl)-thiazol-2-yl]-piperidin-1-yl}-pyrimidine provided herein are found to be cyrstalline solids as further evidenced by their XRPD patterns. In contrast, salts formed from acetic, adipic, L-ascorbic, L-aspartic, citric, formic, gentisic (2,5-dihydroxybenzoic), L-glutamic, glutaric, lactic, maleic, L-malic, phosphoric, and L-tartaric were found to be oils or gels that were difficult to handle and isolate, and would not be suitable for use in bulk preparations. The crystalline besylate, camsylate, esylate, HBr, HCl, mesylate, sulfate, and tosylates salts are therefore superior for use in preparing pharmaceutical salts of 5-ethyl-2-{4-[4-(4-tetrazol-1-yl-phenoxymethyl)-thiazol-2-yl]-piperidin-1-yl}-pyrimidine.

The salts are characterized by a number of solid state techniques such as DSC and TGA. It is understood that melting point temperatures and thermograms can vary depending on instrumentation and the procedures employed, including the heating rate used. Accordingly, the temperature data and graphs disclosed herein are understood to accommodate such variations.

The salts are also characterized by XRPD (x-ray powder diffraction). Relative intensities and peak assignments can vary depending on a number of factors, including sample preparation, mounting, and the instrument and analytical procedure and settings used to obtain the spectrum. The peak assignments described herein are intended to encompass variations of plus or minus 0.5 degrees 2 theta.

Figure 8:
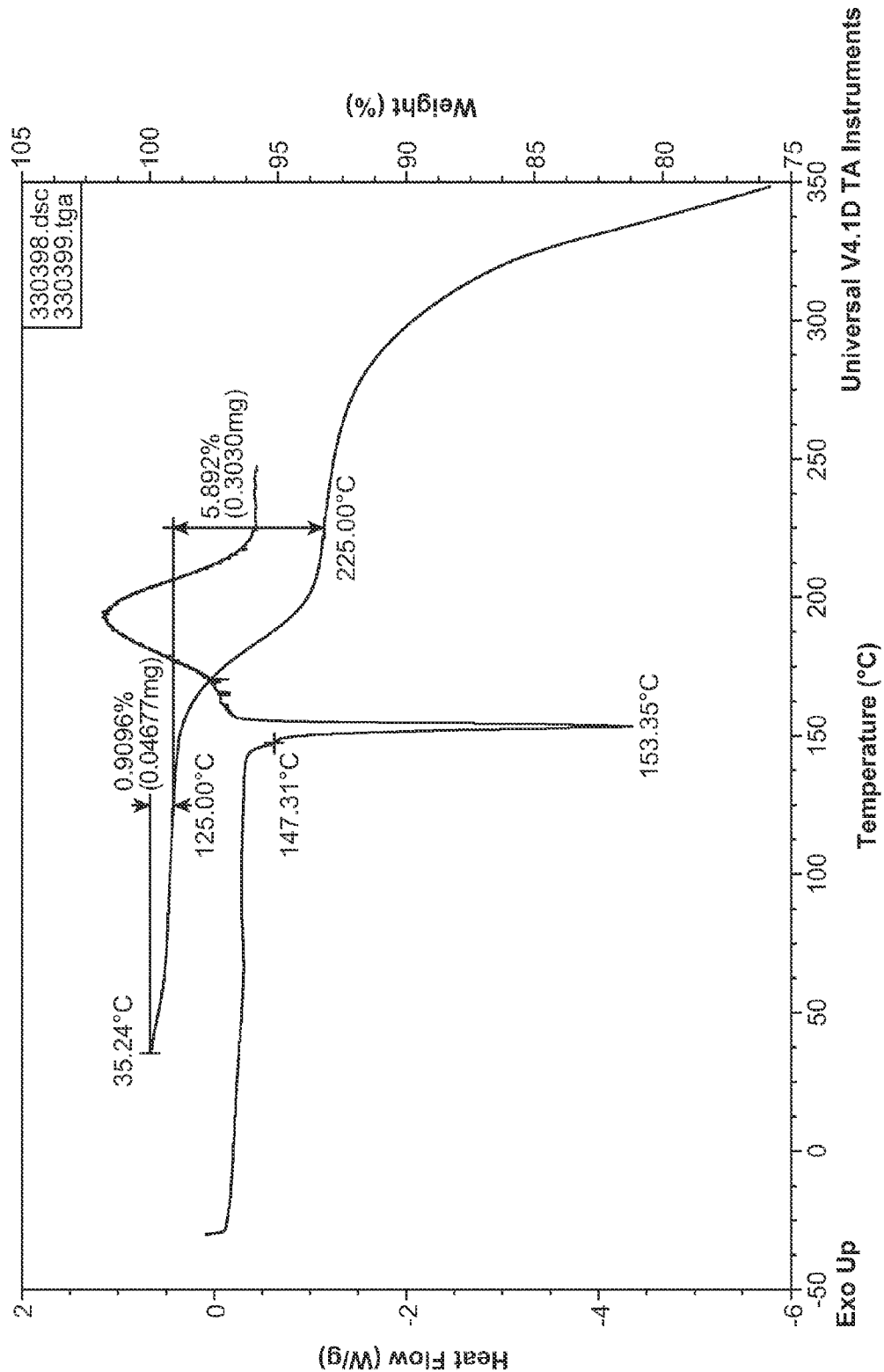
FIG. 8 shows an overlay of the DSC and TGA thermograms of the besylate salt.
Figure 15:
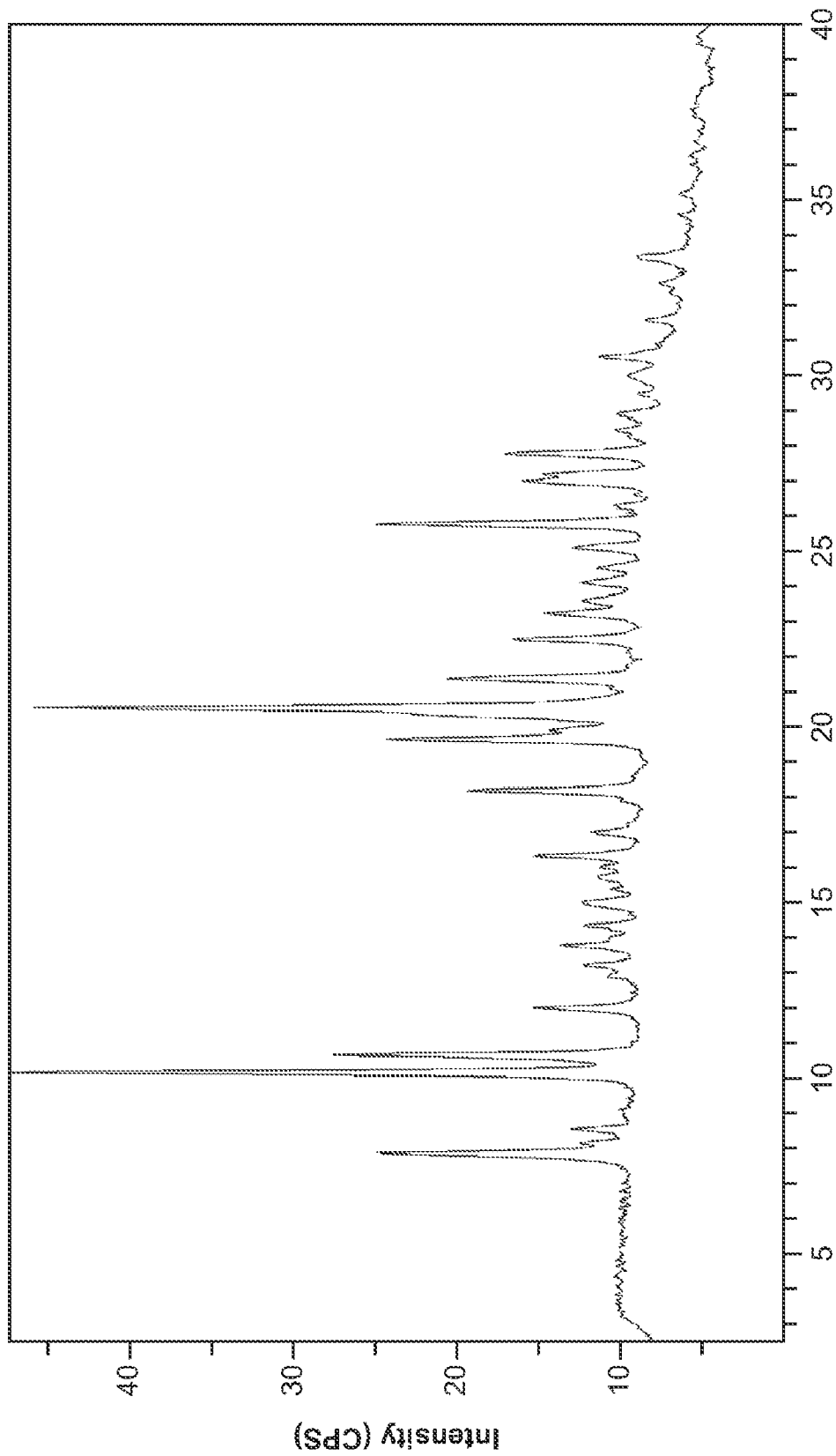
FIG. 15 shows the X-ray powder pattern of the besylate salt.

In one embodiment, provided is a crystalline besyalte salt having a DSC endotherm at about 153° C. In one aspect, the besylate salt has a DSC or TGA thermogram substantially as shown in FIG. 8. In other aspects, the besylate salt has the XRPD pattern substantially as shown in FIG. 15.

Figure 9:
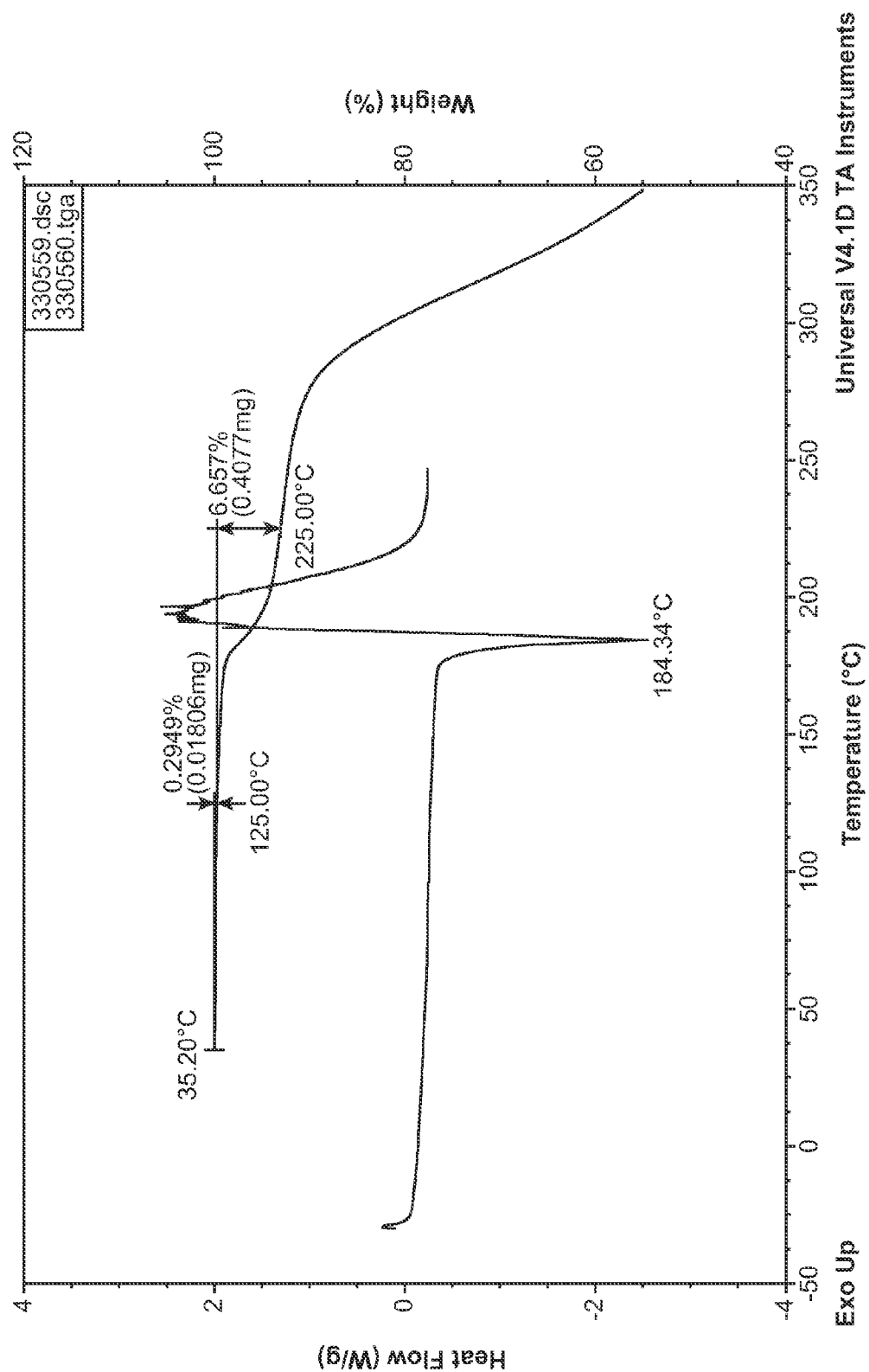
FIG. 9 shows an overlay of the DSC and TGA thermograms of the camsylate salt.
Figure 16:
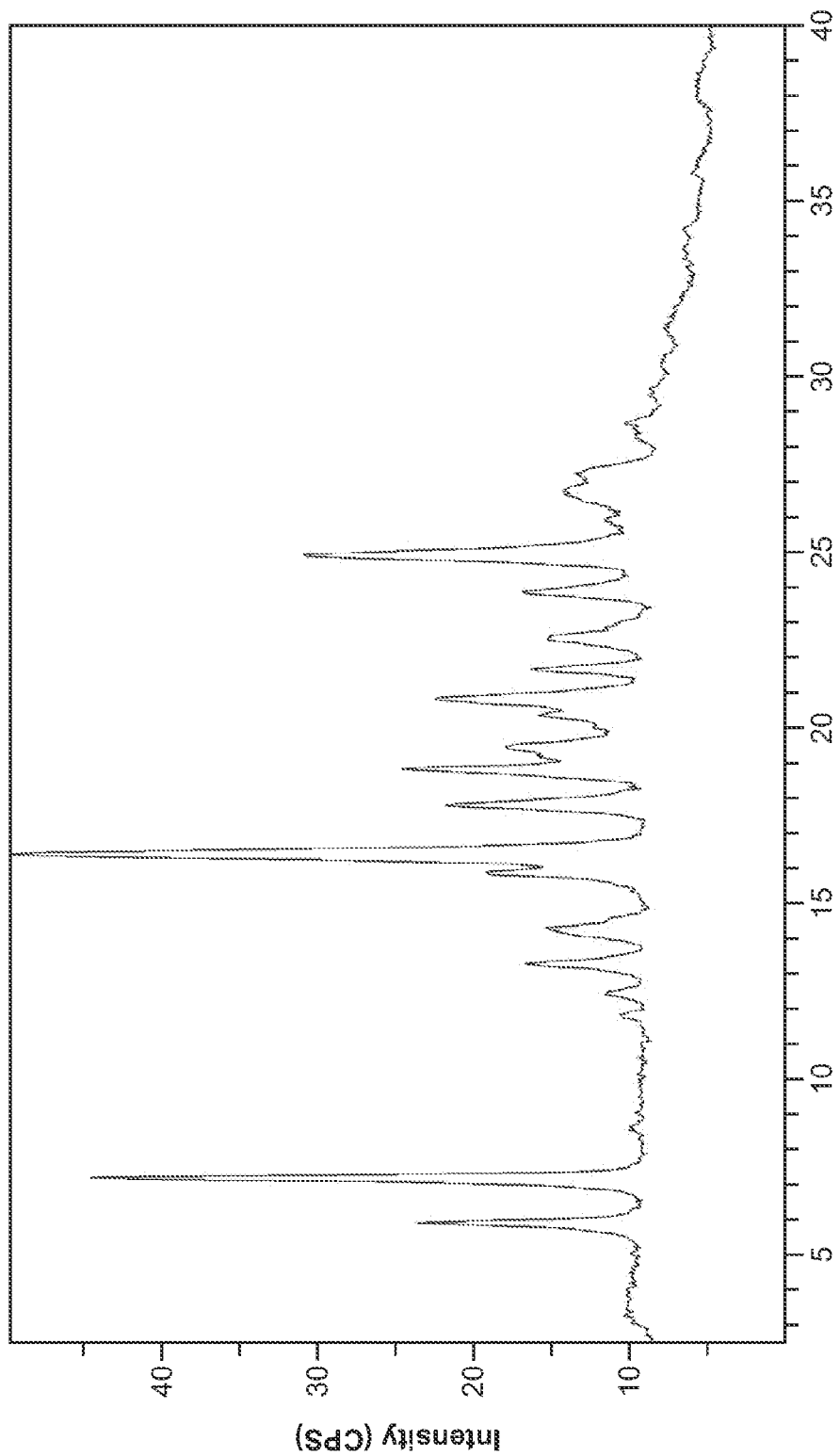
FIG. 16 shows the X-ray powder pattern of the camsylate salt.

In one embodiment, provided is a crystalline camsylate salt having a DSC endotherm at about 184° C. In one aspect, the camsylate salt has a DSC or TGA thermogram substantially as shown in FIG. 9. In other aspects, the camsylate salt has the XRPD pattern substantially as shown in FIG. 16.

Figure 10:
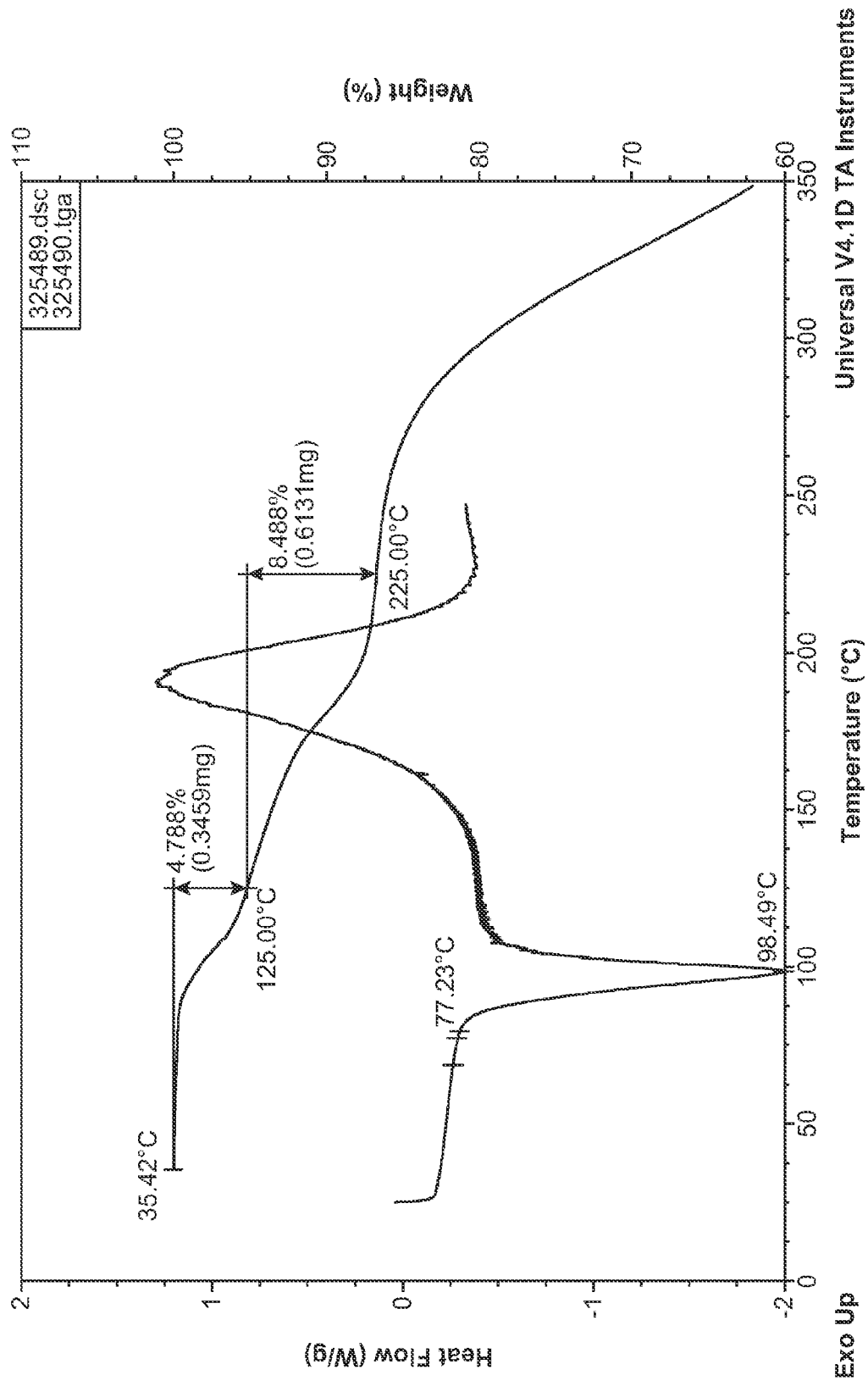
FIG. 10 shows an overlay of the DSC and TGA thermograms of the esylate salt.
Figure 17:
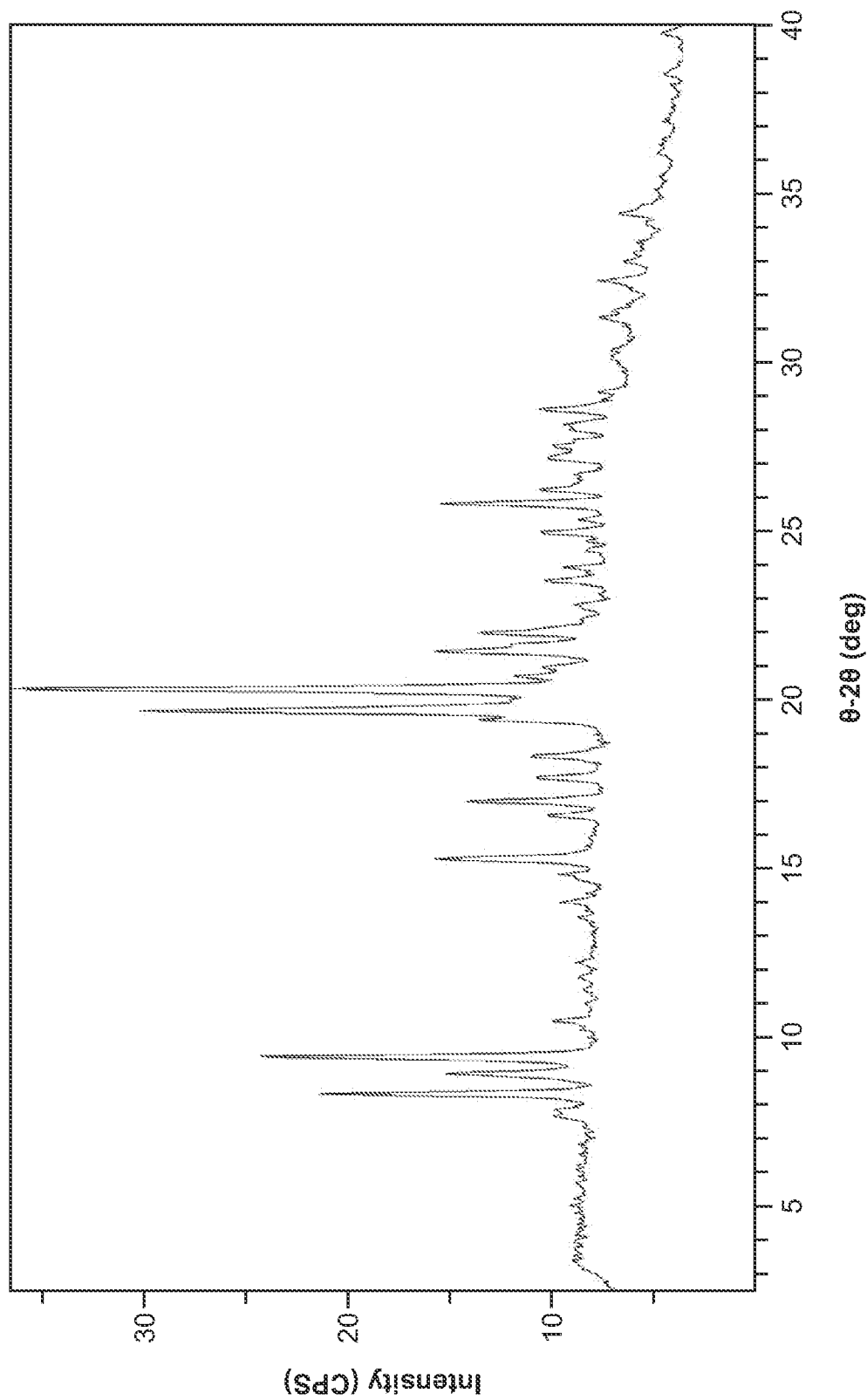
FIG. 17 shows the X-ray powder pattern of the esylate salt.

In one embodiment, provided is a crystalline esylate salt having a DSC endotherm at about 99° C. In one aspect, the esylate salt has a DSC or TGA thermogram substantially as shown in FIG. 10. In other aspects, the esylate salt has the XRPD pattern substantially as shown in FIG. 17.

Figure 11:
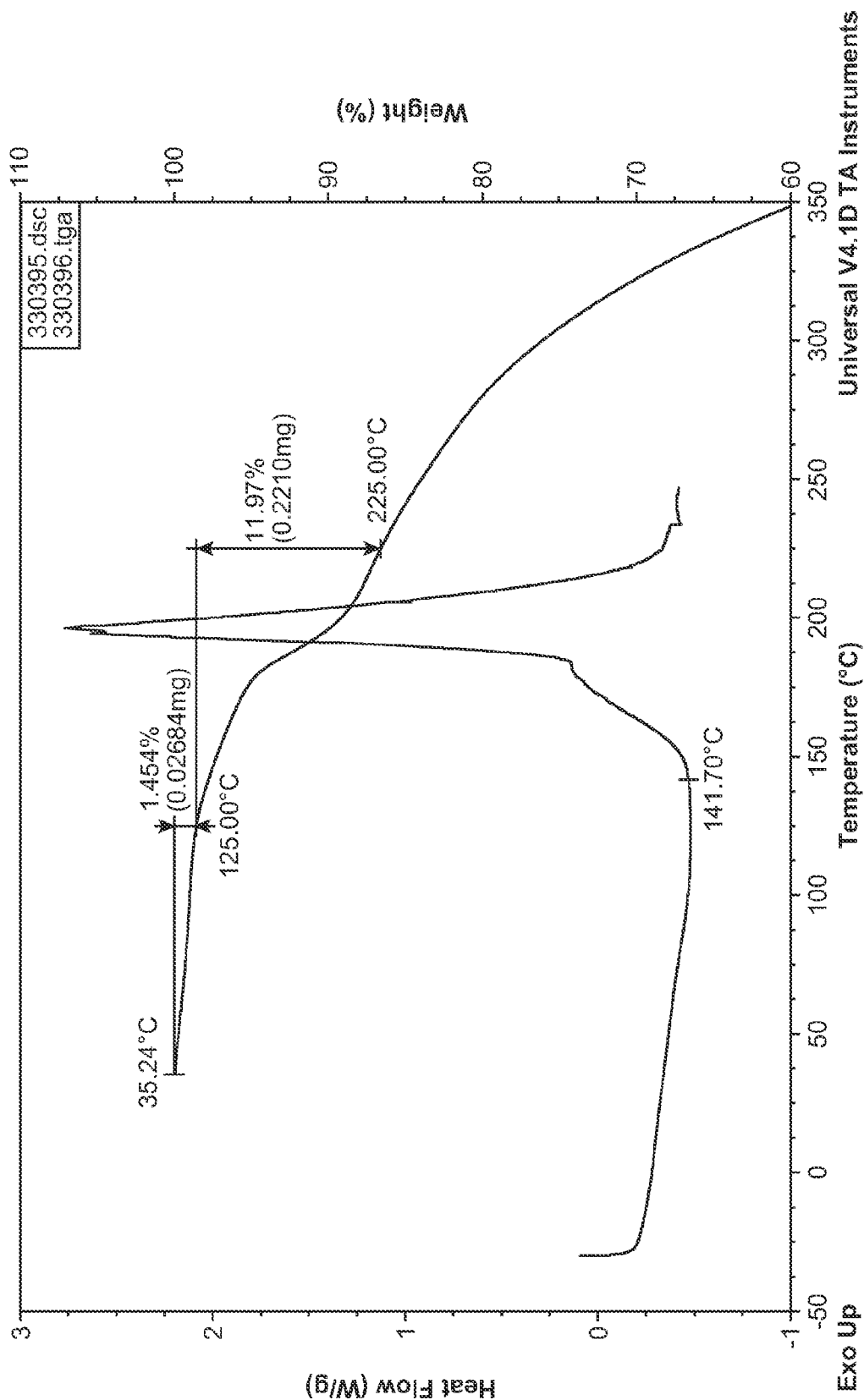
FIG. 11 shows an overlay of the DSC and TGA thermograms of the HBr salt.
Figure 18:
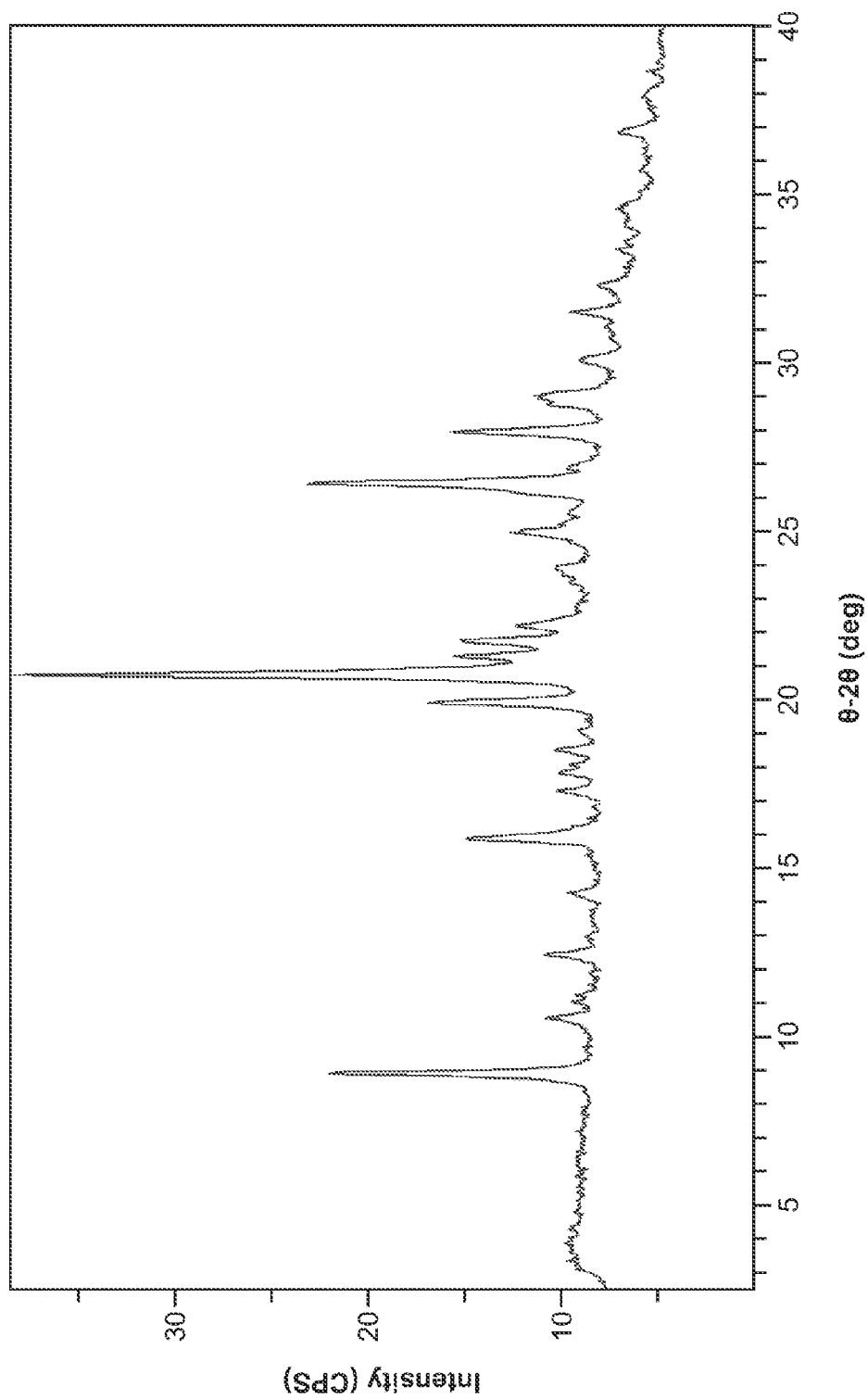
FIG. 18 shows the X-ray powder pattern of the HBr salt.

In one embodiment, provided is a crystalline HBr salt having a DSC endotherm at about 142° C. In one aspect, the HBr salt has a DSC or TGA thermogram substantially as shown in FIG. 11. In other aspects, the HBr salt has the XRPD pattern substantially as shown in FIG. 18.

Figure 12:
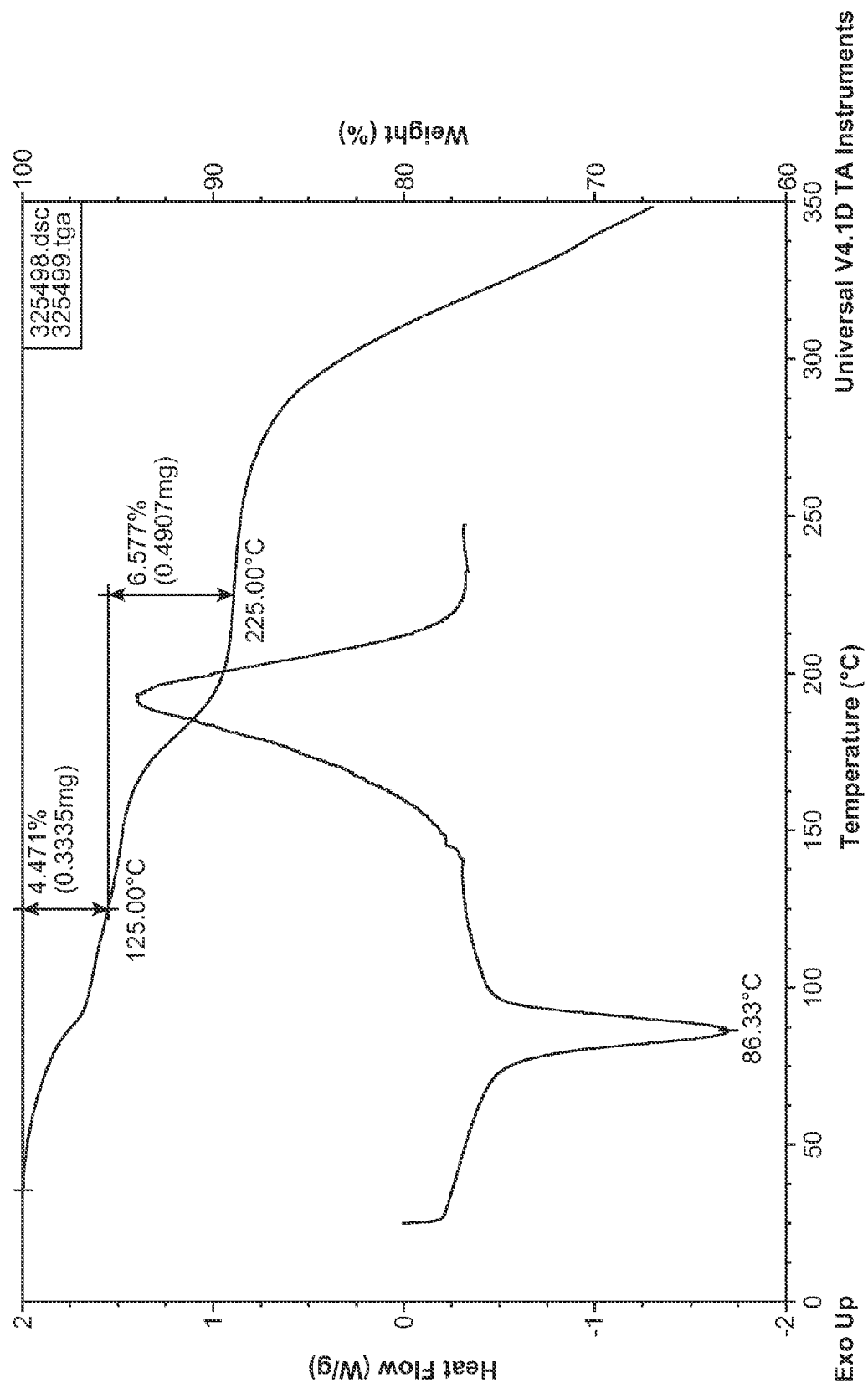
FIG. 12 shows an overlay of the DSC and TGA thermograms of the mesylate salt.
Figure 19:
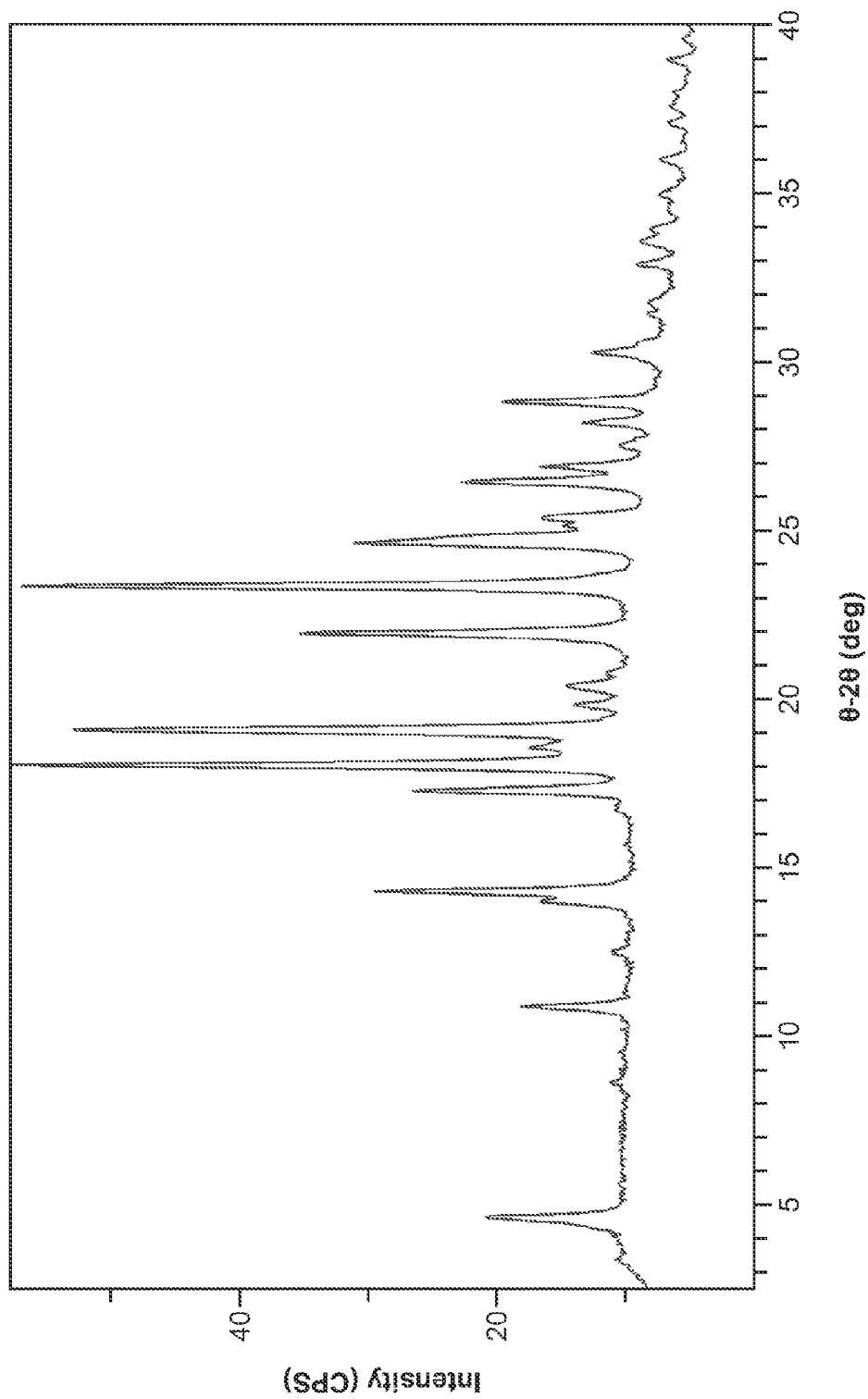
FIG. 19 shows the X-ray powder pattern of the mesylate salt.

In one embodiment, provided is a crystalline mesylate salt having a DSC endotherm at about 86° C. In one aspect, the mesylate salt has a DSC or TGA thermogram substantially as shown in FIG. 12. In other aspects, the mesylate salt has the XRPD pattern substantially as shown in FIG. 19.

Figure 13:
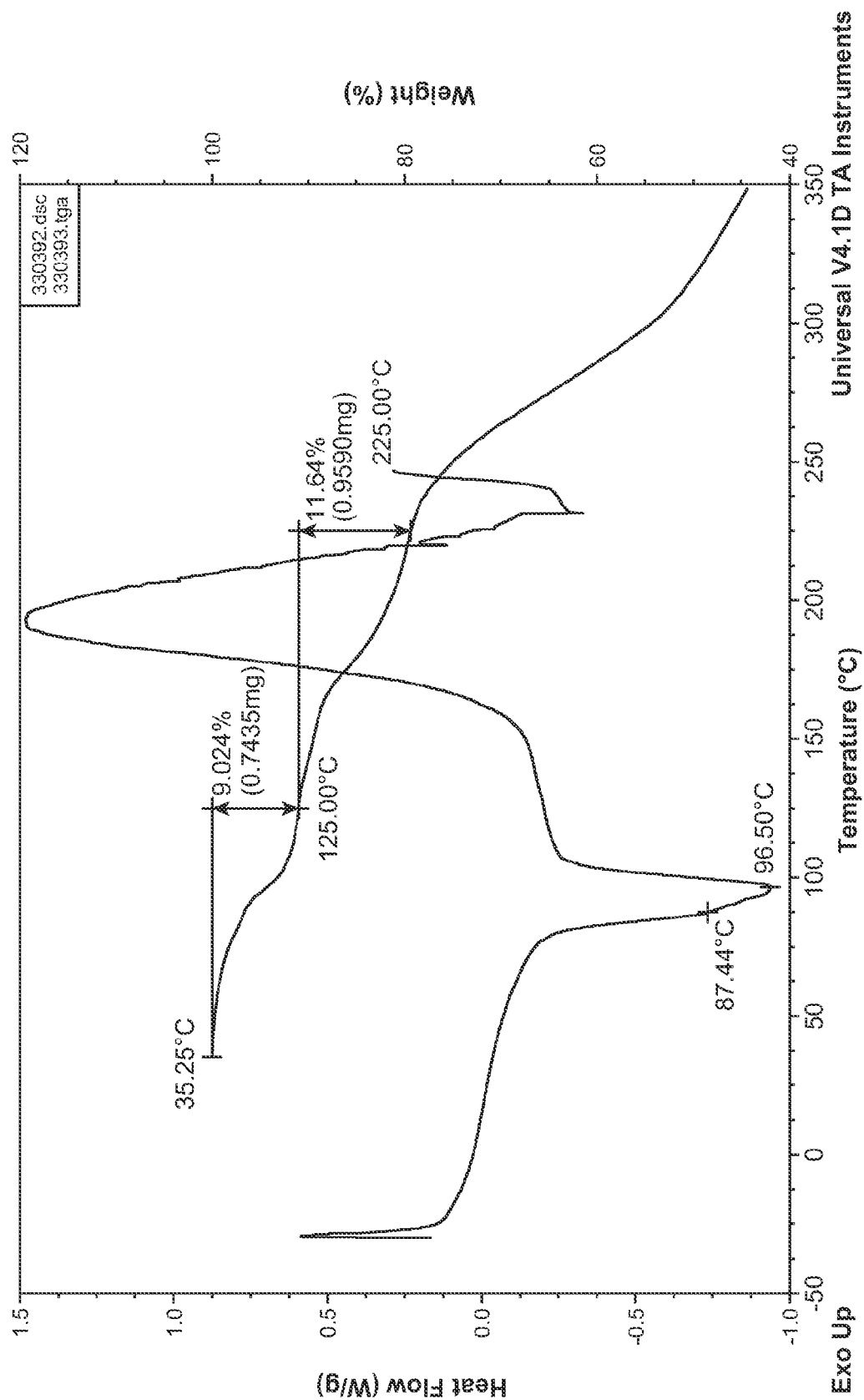
FIG. 13 shows an overlay of the DSC and TGA thermograms of the sulfate salt.
Figure 20:
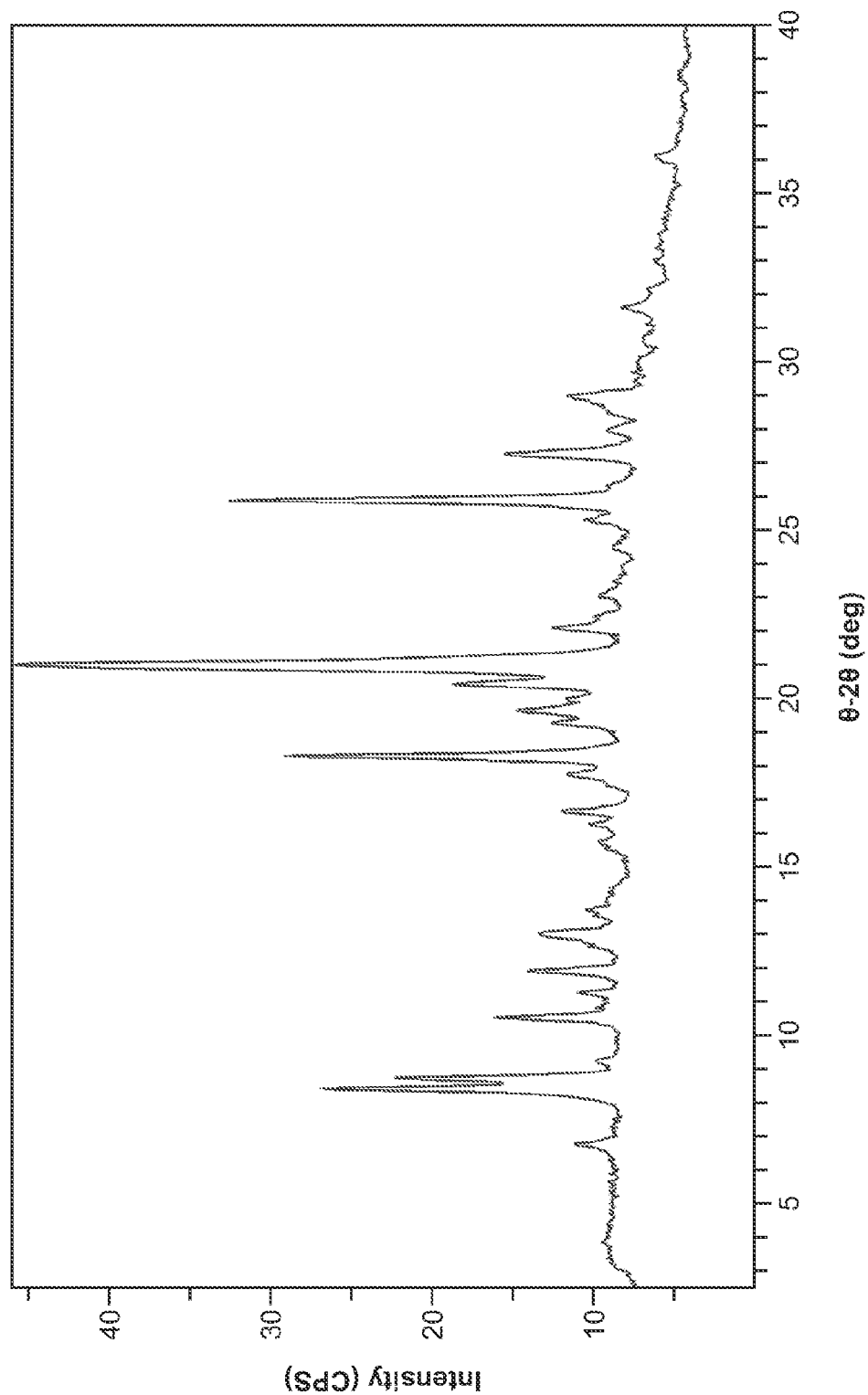
FIG. 20 shows the X-ray powder pattern of the sulfate salt.

In one embodiment, provided is a crystalline sulfate salt having a DSC endotherm at about 97° C. In one aspect, the sulfate salt has a DSC or TGA thermogram substantially as shown in FIG. 13. In other aspects, the sulfate salt has the XRPD pattern substantially as shown in FIG. 20.

Figure 14:
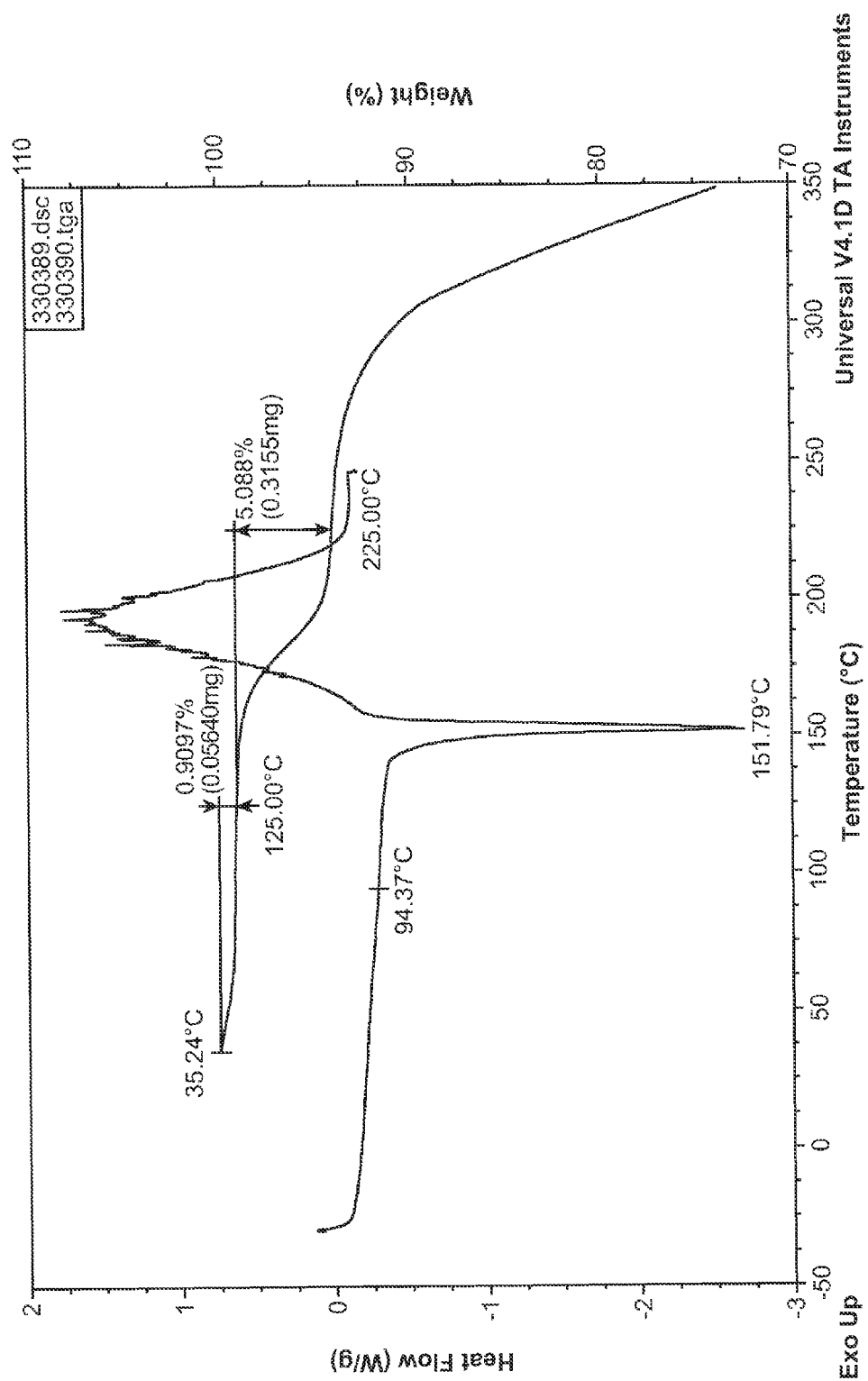
FIG. 14 shows an overlay of the DSC and TGA thermograms of the tosylate salt.
Figure 21:
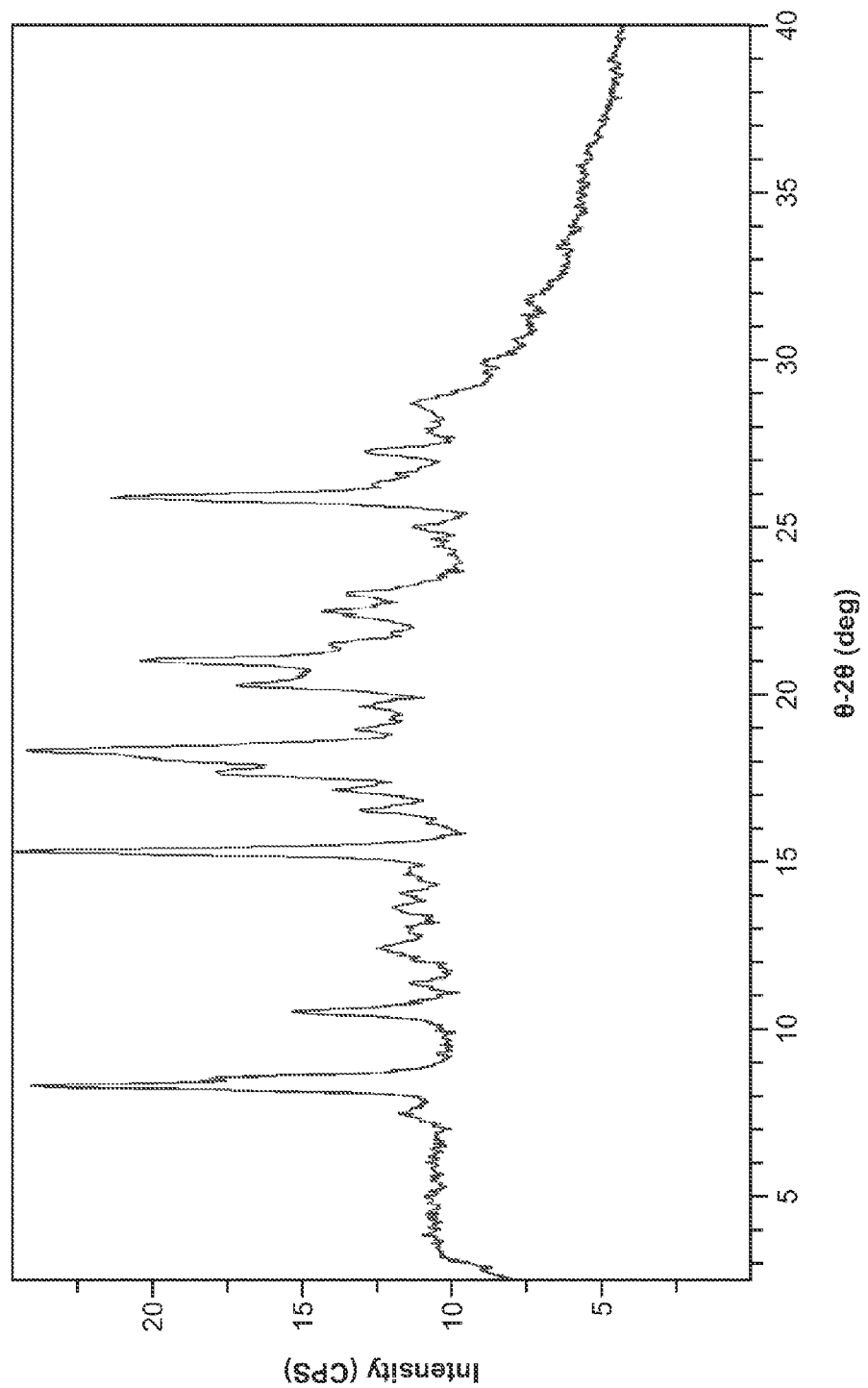
FIG. 21 shows the X-ray powder pattern of the tosylate salt.

In one embodiment, provided is a crystalline tosylate salt having a DSC endotherm at about 94° C. In one aspect, the tosylate salt has a DSC or TGA thermogram substantially as shown in FIG. 14. In other aspects, the tosylate salt has the XRPD pattern substantially as shown in FIG. 21.

In one embodiment, provided is a crystalline HCl salt. The crystalline HCl salts include the crystal "pattern O" described below and those described in the Examples (Table 6). The HCl salt may also contain a polymorph such as Form I or Form II described below or mixtures thereof. The crystalline HCl may also contain trace amounts of solvents such as acetone, ethanol, methanol, and ethyl acetate. In some aspects, the Form I polymorph provide herein is substantially pure and may contain residual acetaone. In some aspects, the Form II polymorph provide herein is substantially pure may contain residual methanol and/or ethyl acetate.

Figure 22:
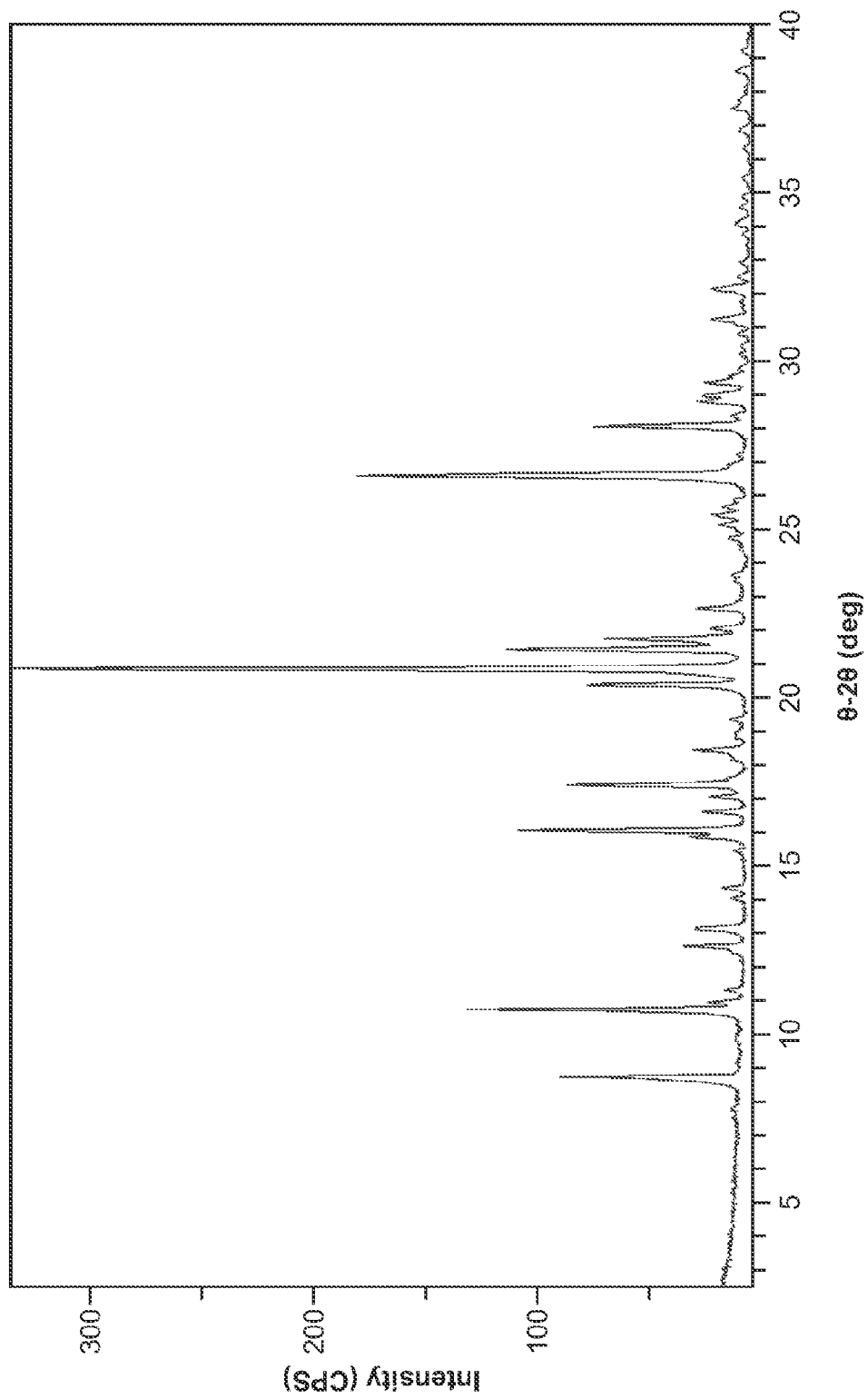
FIG. 22 shows the X-ray powder pattern of the HCl salt (pattern O).

In one embodiment, provided is a crystalline HCl salt (pattern O) containing trace amounts of ethanol, In one aspect, the ratio of EtOH to HCl salt is approximately 1:6. In one aspect, the HCl salt the XRPD pattern substantially as shown in FIG. 22.

Figure 2:
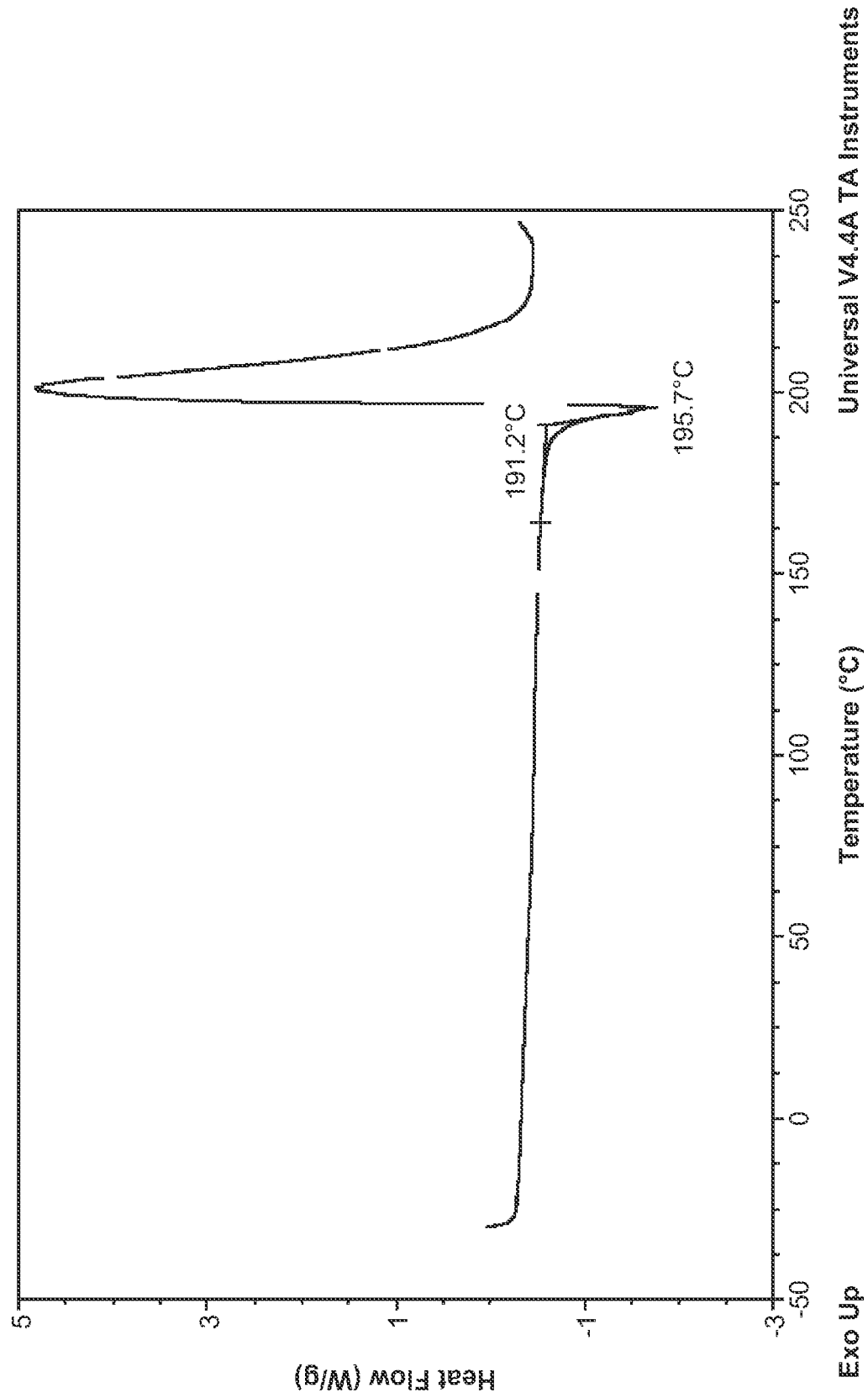
FIG. 2 shows the DSC thermogram of HCl salt Form I.
Figure 3:
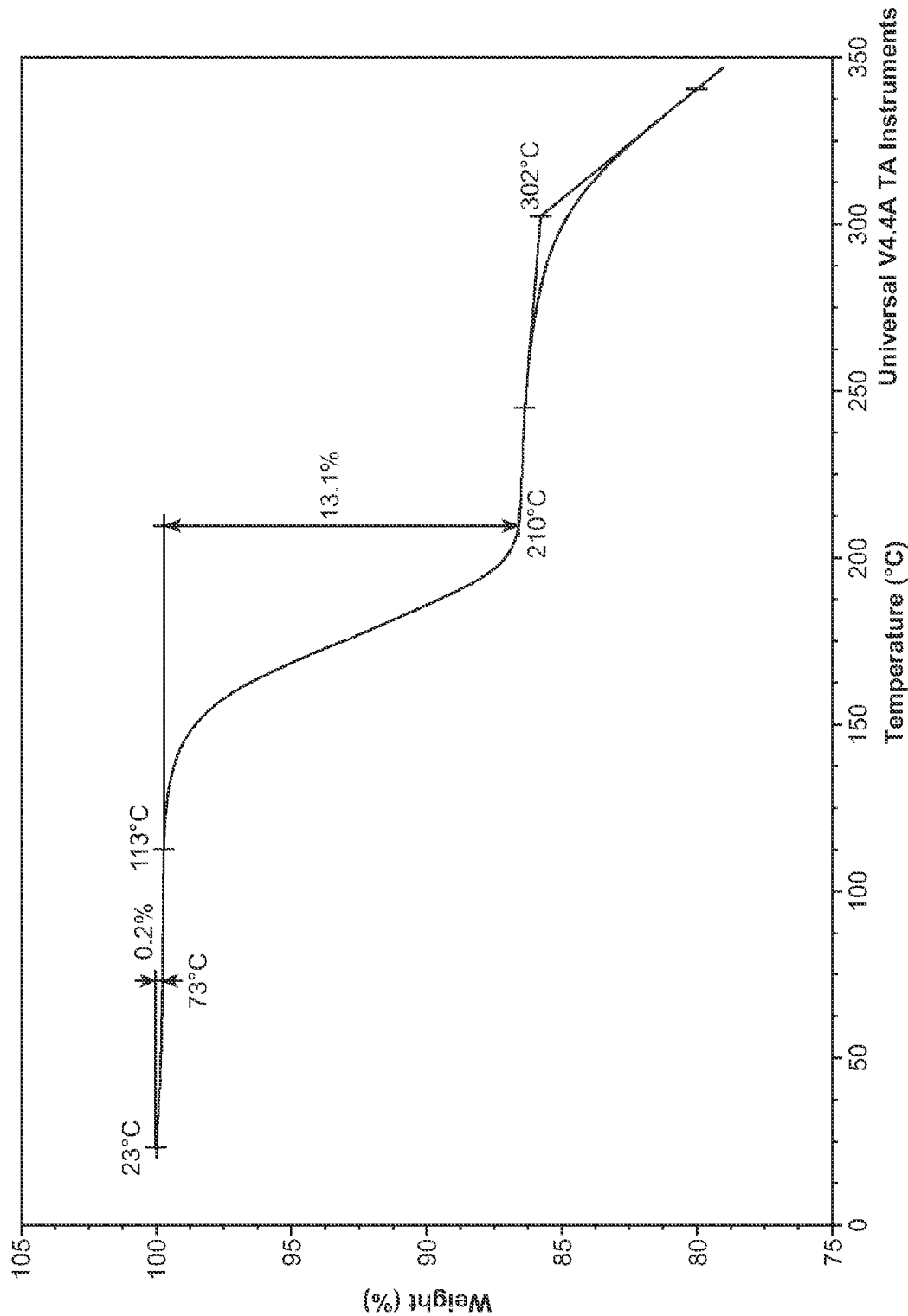
FIG. 3 shows the TGA thermogram of HCl salt Form I.
Figure 4:
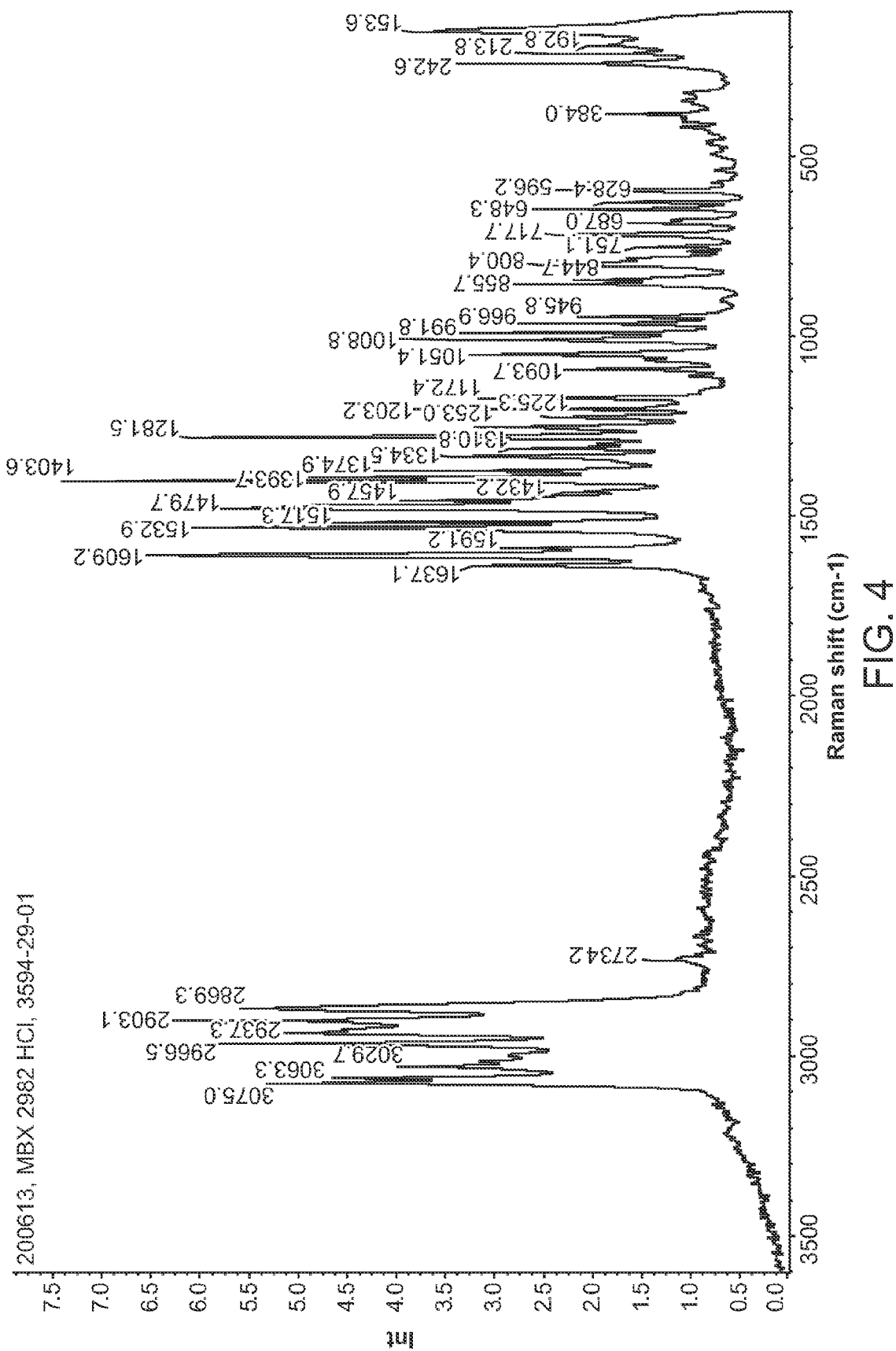
FIG. 4 shows the Raman spectrum of HCl salt Form I.

In one embodiment, provided is polymorph (Form I) HCl salt having a DSC endotherm onset at about 191° C. In one aspect, the Form I polymorph has a DSC thermogram substantially as shown in FIG. 2. In other aspects, the Form I polymorph has a TGA thermogram substantially as shown in FIG. 3. In other aspects, the Form I polymorph has a Raman spectrum substantially as shown in FIG. 4. In other aspects, the Form I polymorph comprises XRPD peaks at degrees 2-theta diffraction angles of about 8.8, 10.8, 16.1, 17.4, 20.4, 20.9, 21.5, 21.7, 26.6, and 28.1. In still other aspects, the Form I polymorph has the XRPD pattern substantially as shown in FIG. 1. Table 1 lists the observed Form 1 XRPD peaks and Table 2 lists the representative peaks, with relative intensities given in both tables. Table 3 lists the observed Raman peaks for Form I.

Figure 5:
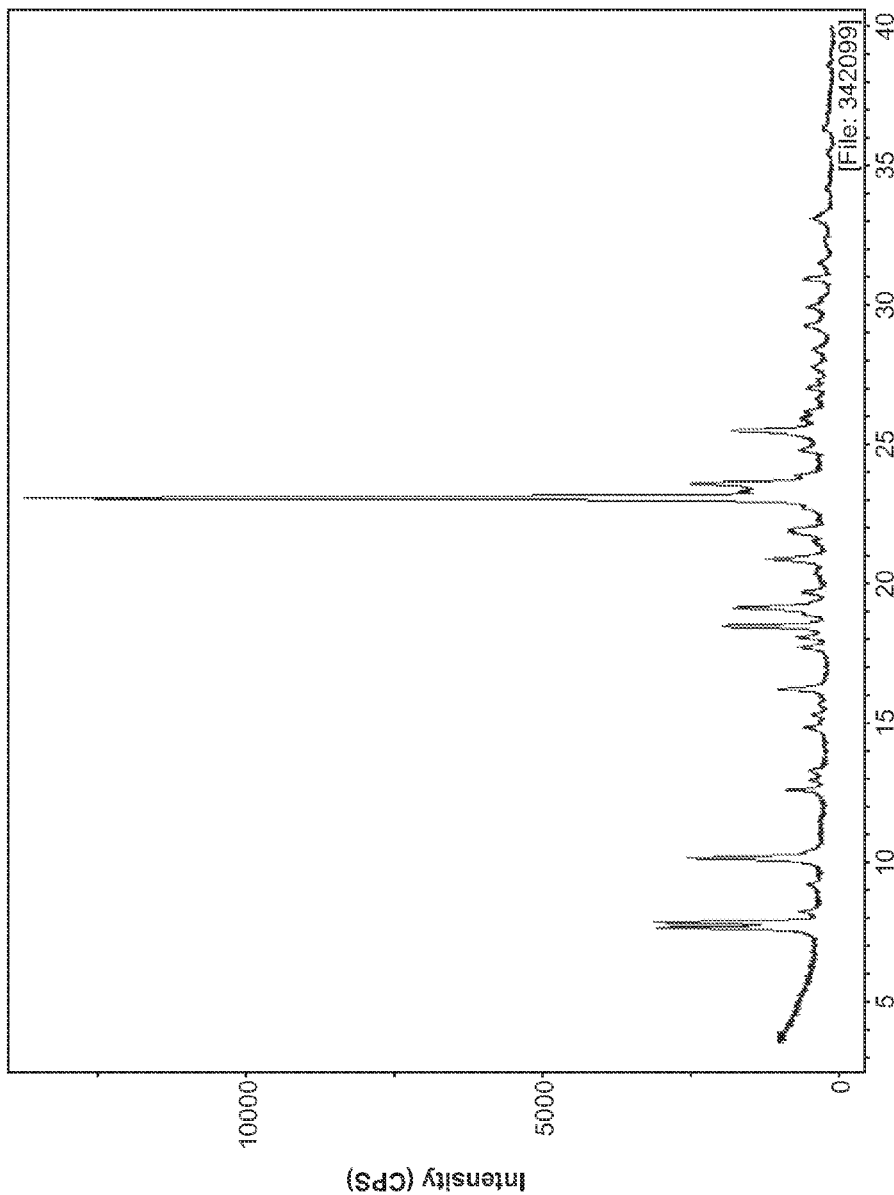
FIG. 5 shows the X-ray powder pattern of HCl salt Form II.
Figure 6:
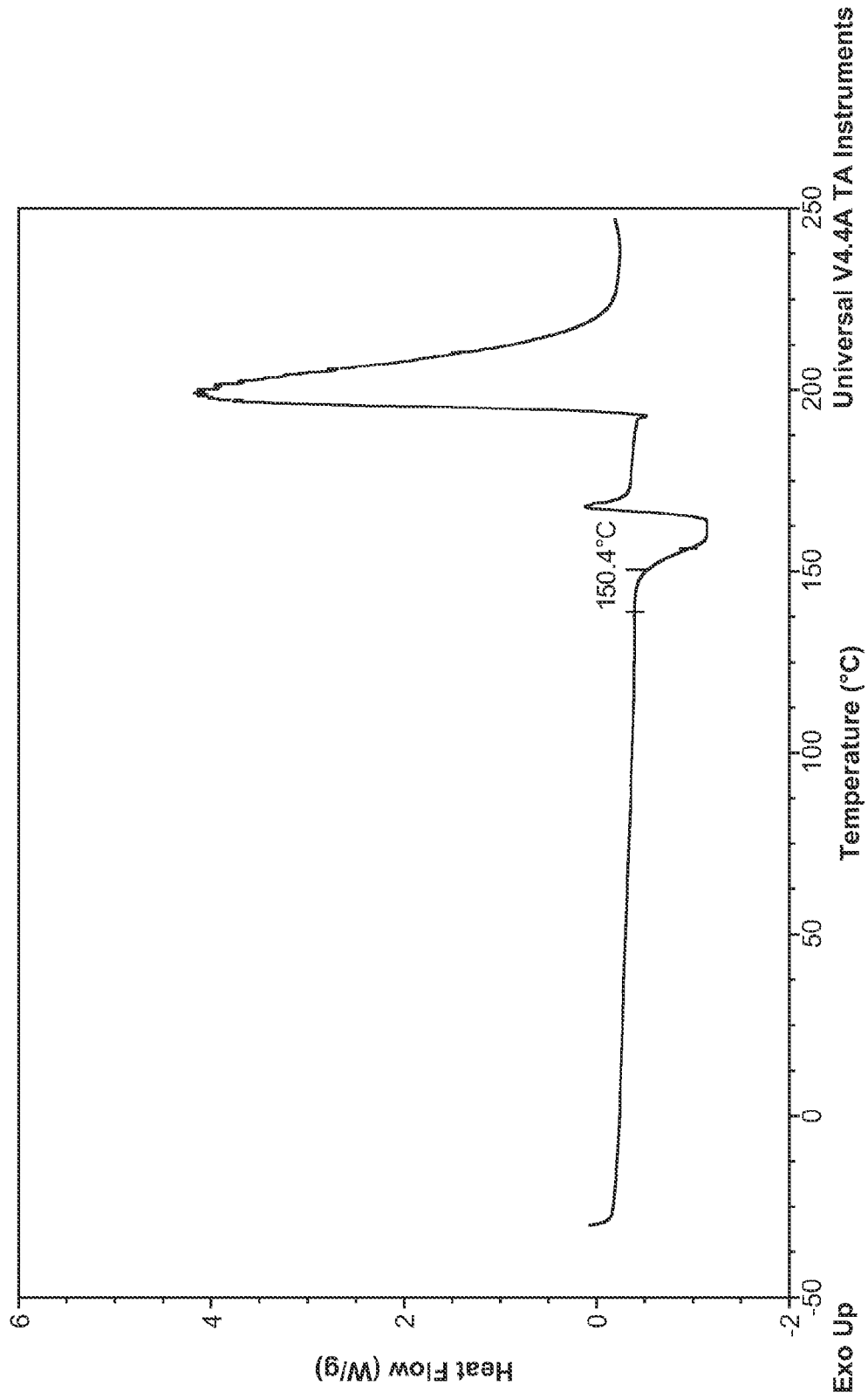
FIG. 6 shows the DSC thermogram of HCl salt Form II.
Figure 7:
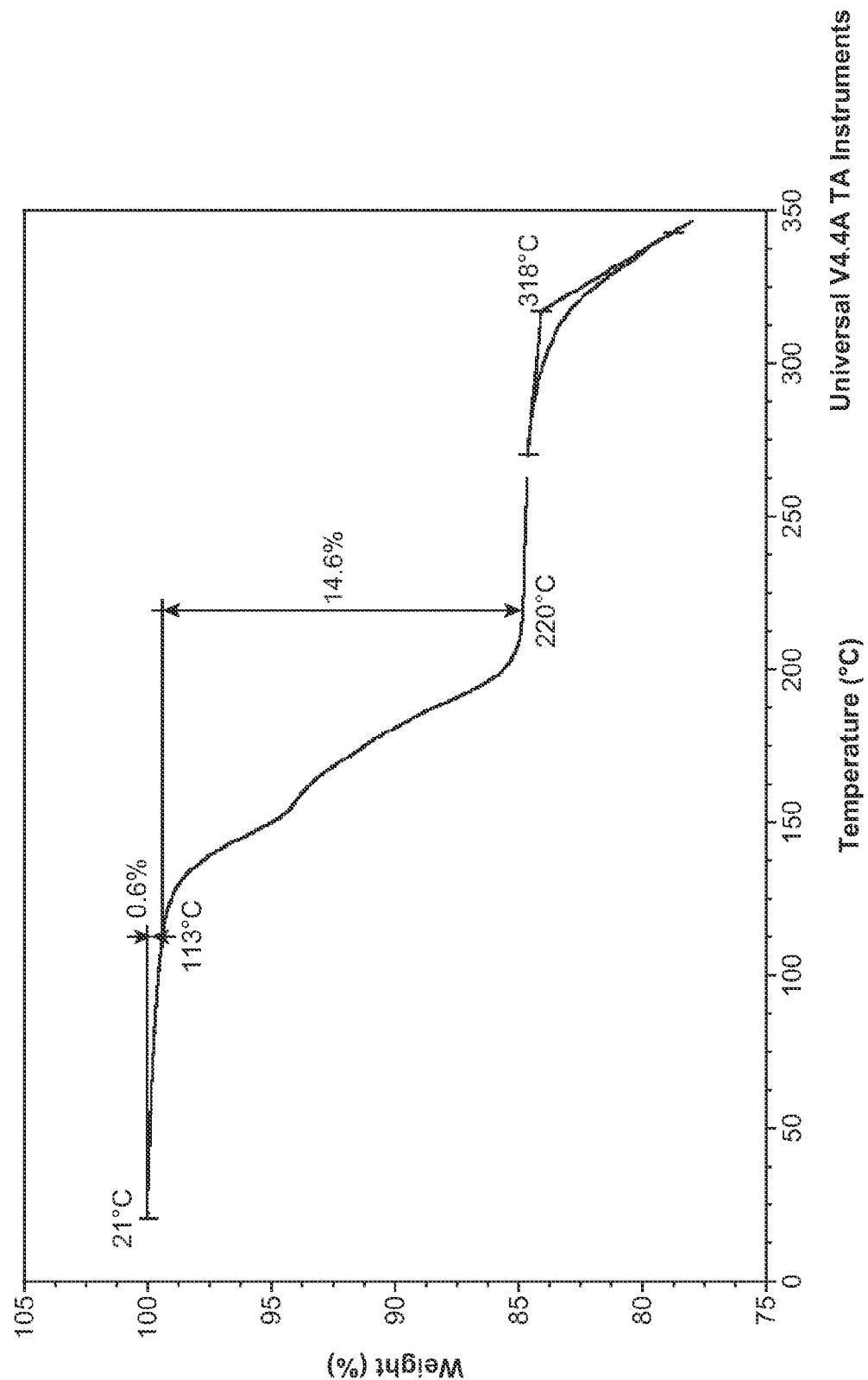
FIG. 7 shows the TGA thermogram of HCl salt Form II.

In one embodiment, provided is polymorph (Form II) HCl salt having a DSC endotherm onset at about 150° C. In one aspect, the Form II polymorph has a DSC thermogram substantially as shown in FIG. 6. In other aspects, the Form II polymorph has a TGA thermogram substantially as shown in FIG. 7. In other aspects, the Form II polymorph comprises XRPD peaks at degrees 2-theta diffraction angles of about 7.8, 10.1, 12.5, 18.4, 19.0, 20.8, 23.0, and 23.5. In still other aspects, the Form II polymorph has the XRPD pattern substantially as shown in FIG. 5. Table 4 lists the observed Form II XRPD peaks and Table 5 lists the representative peaks, with relative intensities given in both tables.

In the Tables below, the location of the peaks were automatically determined using PatternMatch™ 3.0.1 software and rounded to one or two significant figures after the decimal point based upon the above criteria. Peak position variabilities are given to within ±0.10° 2 theta based upon recommendations outlined in the United States Pharmacopeia (USP 32, NF 27, Vol. 1, pg. 392, 2009) discussion of variability in x-ray powder diffraction. The accuracy and precision associated with any particular measurement reported herein has not been determined. Moreover, third party measurements on independently prepared samples on different instruments may lead to variability which is greater than ±0.10° 2 theta (for example ±0.50° 2 theta or more).

TABLE 1

Observed XRPD peaks for HCl polymorph Form I.

| °2θ | d space (Å) | Intensity (%) |
|---|---|---|
| 8.76 ± 0.10 | 10.092 ± 0.116 | 24 |
| 10.78 ± 0.10 | 8.204 ± 0.077 | 40 |
| 10.98 ± 0.10 | 8.054 ± 0.074 | 5 |
| 11.34 ± 0.10 | 7.806 ± 0.069 | 3 |
| 12.66 ± 0.10 | 6.994 ± 0.055 | 8 |
| 13.14 ± 0.10 | 6.738 ± 0.051 | 7 |
| 14.06 ± 0.10 | 6.299 ± 0.045 | 2 |
| 14.38 ± 0.10 | 6.161 ± 0.043 | 3 |
| 15.48 ± 0.10 | 5.724 ± 0.037 | 2 |
| 15.88 ± 0.10 | 5.581 ± 0.035 | 8 |
| 16.10 ± 0.10 | 5.506 ± 0.034 | 31 |
| 16.65 ± 0.10 | 5.325 ± 0.032 | 7 |
| 17.08 ± 0.10 | 5.190 ± 0.030 | 5 |
| 17.45 ± 0.10 | 5.082 ± 0.029 | 26 |
| 18.15 ± 0.10 | 4.887 ± 0.027 | 2 |
| 18.30 ± 0.10 | 4.847 ± 0.026 | 3 |
| 18.45 ± 0.10 | 4.808 ± 0.026 | 6 |
| 18.81 ± 0.10 | 4.719 ± 0.025 | 1 |
| 19.39 ± 0.10 | 4.578 ± 0.024 | 2 |
| 20.39 ± 0.10 | 4.355 ± 0.021 | 23 |
| 20.88 ± 0.10 | 4.255 ± 0.020 | 100 |
| 21.46 ± 0.10 | 4.140 ± 0.019 | 34 |
| 21.76 ± 0.10 | 4.084 ± 0.019 | 20 |
| 22.06 ± 0.10 | 4.029 ± 0.018 | 5 |
| 22.67 ± 0.10 | 3.923 ± 0.017 | 6 |
| 23.49 ± 0.10 | 3.788 ± 0.016 | 2 |
| 23.69 ± 0.10 | 3.757 ± 0.016 | 2 |
| 24.37 ± 0.10 | 3.652 ± 0.015 | 1 |
| 24.74 ± 0.10 | 3.599 ± 0.014 | 3 |
| 24.99 ± 0.10 | 3.563 ± 0.014 | 2 |
| 25.16 ± 0.10 | 3.540 ± 0.014 | 4 |
| 25.44 ± 0.10 | 3.501 ± 0.014 | 5 |
| 25.67 ± 0.10 | 3.470 ± 0.013 | 4 |
| 25.86 ± 0.10 | 3.446 ± 0.013 | 2 |
| 26.61 ± 0.10 | 3.350 ± 0.012 | 53 |
| 28.06 ± 0.10 | 3.180 ± 0.011 | 22 |
| 28.35 ± 0.10 | 3.148 ± 0.011 | 3 |
| 28.80 ± 0.10 | 3.100 ± 0.011 | 7 |
| 29.02 ± 0.10 | 3.077 ± 0.010 | 6 |
| 29.37 ± 0.10 | 3.041 ± 0.010 | 6 |

TABLE 2

Representative XRPD peaks for HCl polymorph Form I.

| °2θ | d space (Å) | Intensity (%) |
|---|---|---|
| 8.76 ± 0.10 | 10.092 ± 0.116 | 24 |
| 10.78 ± 0.10 | 8.204 ± 0.077 | 40 |
| 16.10 ± 0.10 | 5.506 ± 0.034 | 31 |
| 17.45 ± 0.10 | 5.082 ± 0.029 | 26 |
| 20.39 ± 0.10 | 4.355 ± 0.021 | 23 |
| 20.88 ± 0.10 | 4.255 ± 0.020 | 100 |
| 21.46 ± 0.10 | 4.140 ± 0.019 | 34 |
| 21.76 ± 0.10 | 4.084 ± 0.019 | 20 |
| 26.61 ± 0.10 | 3.350 ± 0.012 | 53 |
| 28.06 ± 0.10 | 3.180 ± 0.011 | 22 |

TABLE 3

Observed Raman peaks for HCl polymorph Form I (cm$^{-1}$)

| 154 | 193 | 214 | 243 |
|---|---|---|---|
| 324 | 346 | 384 | 420 |
| 460 | 467 | 495 | 539 |
| 573 | 596 | 628 | 648 |
| 680 | 687 | 718 | 751 |
| 766 | 787 | 800 | 845 |
| 856 | 946 | 967 | 992 |
| 1009 | 1051 | 1068 | 1094 |
| 1110 | 1172 | 1203 | 1225 |

TABLE 3-continued

Observed Raman peaks for HCl polymorph Form I (cm$^{-1}$)

| | | | |
|---|---|---|---|
| 1253 | 1282 | 1300 | 1311 |
| 1334 | 1375 | 1394 | 1404 |
| 1432 | 1458 | 1474 | 1480 |
| 1517 | 1533 | 1591 | 1609 |
| 1637 | 2734 | 2869 | 2903 |
| 2928 | 2937 | 2967 | 2999 |
| 3015 | 3030 | 3063 | 3075 |

TABLE 4

Observed XRPD peaks for HCl polymorph Form II.

| °2θ | d space (Å) | Intensity (%) |
|---|---|---|
| 7.63 ± 0.10 | 11.593 ± 0.154 | 23 |
| 7.79 ± 0.10 | 11.345 ± 0.147 | 43 |
| 8.14 ± 0.10 | 10.857 ± 0.135 | 6 |
| 9.18 ± 0.10 | 9.634 ± 0.106 | 5 |
| 10.07 ± 0.10 | 8.788 ± 0.088 | 41 |
| 10.35 ± 0.10 | 8.547 ± 0.083 | 15 |
| 12.54 ± 0.10 | 7.059 ± 0.057 | 50 |
| 12.87 ± 0.10 | 6.877 ± 0.054 | 5 |
| 13.24 ± 0.10 | 6.687 ± 0.051 | 18 |
| 14.78 ± 0.10 | 5.994 ± 0.041 | 7 |
| 14.98 ± 0.10 | 5.915 ± 0.040 | 7 |
| 15.20 ± 0.10 | 5.831 ± 0.038 | 18 |
| 15.61 ± 0.10 | 5.675 ± 0.036 | 3 |
| 15.91 ± 0.10 | 5.569 ± 0.035 | 6 |
| 16.12 ± 0.10 | 5.500 ± 0.034 | 17 |
| 17.69 ± 0.10 | 5.015 ± 0.028 | 28 |
| 17.97 ± 0.10 | 4.936 ± 0.027 | 28 |
| 18.39 ± 0.10 | 4.825 ± 0.026 | 100 |
| 18.82 ± 0.10 | 4.715 ± 0.025 | 21 |
| 19.01 ± 0.10 | 4.669 ± 0.024 | 85 |
| 19.27 ± 0.10 | 4.605 ± 0.024 | 14 |
| 19.67 ± 0.10 | 4.512 ± 0.023 | 11 |
| 20.14 ± 0.10 | 4.409 ± 0.022 | 9 |
| 20.81 ± 0.10 | 4.268 ± 0.020 | 58 |
| 21.41 ± 0.10 | 4.150 ± 0.019 | 18 |
| 21.83 ± 0.10 | 4.071 ± 0.019 | 35 |
| 22.20 ± 0.10 | 4.005 ± 0.018 | 6 |
| 22.65 ± 0.10 | 3.926 ± 0.017 | 25 |
| 23.03 ± 0.10 | 3.861 ± 0.017 | 83 |
| 23.27 ± 0.10 | 3.823 ± 0.016 | 35 |
| 23.54 ± 0.10 | 3.780 ± 0.016 | 47 |
| 23.84 ± 0.10 | 3.733 ± 0.016 | 11 |
| 24.45 ± 0.10 | 3.640 ± 0.015 | 12 |
| 24.67 ± 0.10 | 3.609 ± 0.014 | 22 |
| 24.94 ± 0.10 | 3.570 ± 0.014 | 12 |
| 25.46 ± 0.10 | 3.499 ± 0.014 | 36 |
| 25.87 ± 0.10 | 3.443 ± 0.013 | 15 |
| 26.08 ± 0.10 | 3.417 ± 0.013 | 17 |
| 26.53 ± 0.10 | 3.360 ± 0.012 | 9 |
| 26.89 ± 0.10 | 3.315 ± 0.012 | 8 |
| 27.23 ± 0.10 | 3.275 ± 0.012 | 8 |
| 27.66 ± 0.10 | 3.225 ± 0.011 | 19 |
| 28.40 ± 0.10 | 3.143 ± 0.011 | 10 |
| 29.17 ± 0.10 | 3.062 ± 0.010 | 13 |
| 29.87 ± 0.10 | 2.991 ± 0.010 | 11 |

TABLE 5

Representative XRPD peaks for HCl polymorph Form II.

| °2θ | d space (Å) | Intensity (%) |
|---|---|---|
| 7.78 ± 0.10 | 11.369 ± 0.148 | 42 |
| 10.07 ± 0.10 | 8.788 ± 0.088 | 41 |
| 12.54 ± 0.10 | 7.059 ± 0.057 | 50 |
| 18.37 ± 0.10 | 4.829 ± 0.026 | 100 |
| 19.01 ± 0.10 | 4.669 ± 0.024 | 86 |
| 20.81 ± 0.10 | 4.268 ± 0.020 | 59 |
| 23.03 ± 0.10 | 3.861 ± 0.017 | 84 |
| 23.54 ± 0.10 | 3.780 ± 0.016 | 48 |

The crystalline salts disclosed herein may be prepared by precipitation from organic or mixed organic solvents and may also be prepared from organic/aqueous solvents. Suitable organic solvents include acetone, acetonitrile, dichloromethane, diethyl ether, ethyl acetate, ethanol, heptane, hexane, hexafluoroisopropanol, isopropyl alcohol, isopropyl ether, methyl ethyl ketone, methanol, methyl-tert-butyl ether, 2,2,2-trifluoroethanol, and tetrahydrofuran.

The HCl salt (Form I) can generally be prepared by addition of HCl to the free base at elevated temperatures in solvent such as acetone, acetonitrile, ethanol/ethyl acetate, methanol/ethyl acetate and THF, optionally followed by further crystallizations in acetone. The HCl salt (Form II) can generally be prepared by crystallizations in methanol. The methanol solution may optionally contain other solvents such as ethyl acetate or acetone.

Illustrative, non-limiting examples of such preparations are given in the Example section below. One of skill in the art, having possession of this disclosure, will be able to modify the examples to come up with alternate crystallization methods and will be able to determine whether such methods are capable of producing the desired crystalline salt.

In accordance with one embodiment of the invention, provided are pharmaceutical compositions comprising one or more crystalline salts as described herein. In other embodiments, provided are uses of the crystalline salts in the preparation of medicaments and their use in treating a disease selected from the group consisting of Type I diabetes, Type II diabetes and metabolic syndrome. The salts may also be used in a combination therapy with a DPP IV inhibitor.

In one embodiment, provided is a method for one or more of stimulating insulin production, stimulating glucose-dependent insulin secretion, lowering blood glucose, or lowering blood triglyceride levels, said method comprising administering to a subject in need of such treatment an effective amount of a crystalline salt as described herein.

The DPP IV inhibitors useful in the present invention are sitagliptin (Merck), vildagliptin (Novartis), BMS-477118 (saxagliptin) (Bristol-Myers Squibb), R1438 (amino-methylpyridine) (Roche), NVP DPP728 (Novartis), PSN9301 (Prosidion), P32/98 (isoleucine thiozolidide) (Probiodrug), GSK823093C (Denagliptin) (Glaxo Smithkline), SYR-322 (Alogliptin) (Takeda), N,N-7201 (NovoNordisk), ALS2-0426 (Alantos). (Green B D, Flatt P R, Bailey C J, Dipeptidyl peptidase IB (DPP IV) inhibitors: a newly emerging drug class for the treatment of Type II diabetes, *Diabetes Vasc Dis Res* 2006, 3:159-165) Preferred DPP IV inhibitors are sitagliptin, vildagliptin, Denagliptin, saxagliptin, and alogliptin). Even more preferred DPP IV inhibitors are sitagliptin and vildagliptin. Sitagliptin is an approved pharmaceutical marketed as Januvia™, and vildagliptin is an approved pharmaceutical marked as Galvus™.

The crystalline salt and DPP IV inhibitor are administered in a single dosage or in separate dosages. The single dosage is administered once a day or multiple times a day. When administered as separate dosages, the dosages can be administered once a day or multiple times a day.

In one embodiment, when the salt and the DPP IV inhibitor are administered in a single dosage, the salt and DPP IV inhibitor are formulated as a medicament into a single pill, single table, or a single capsule. When the salt and DPP IV inhibitor are administered in separate dosages, the salt is formulated as a medicament into a pill, tablet or capsule and the DPP IV inhibitor is formulated into a separate pill or capsule.

When the salt and DPP IV inhibitor are administered in separate dosages, the salt can be administered first and the DPP IV inhibitor can be administered next, following administration of the salt. Alternatively, the DPP IV inhibitor can be administered first and the salt can be administered next, following administration of the DPP IV inhibitor. The time between the sequential first administration and the second administration can be varied by a skilled practitioner. In one embodiment, the first administration (the salt or DPP IV inhibitor), is followed immediately by the second administration (the salt or DPP IV inhibitor). In another embodiment, the second administration is within 2 minutes, 5 minutes, 10 minutes, 15 minutes, 30 minutes, or 60 minutes, 1 hour, 2 hours, 3 hours, 4 hours, 5 hours, 6 hours, 7 hours, 8 hours, 9 hours, 10 hours, 11 hours, or 12 hours following the first administration. Yet another embodiment provides for the administration to a subject the salt and/or DPP IV inhibitor in the morning followed by administration to the previously treated subject the salt and/or DPP IV inhibitor in the evening. In another embodiment, the salt and DPP IV inhibitor are preferably administered once a day.

Another aspect of this invention provides methods of lowering blood levels of glucose in a subject by administering the salt and a DPP IV inhibitor. The method comprises administering an effective amount of the salt and DPP IV inhibitor to the mammal. The method further comprises steps to measure blood glucose levels before and after administration of the salt and DPP IV inhibitor. Blood glucose levels are easily measured by numerous commercially available glucose monitoring devices that measure blood glucose from samples of blood or urine, or as taught herein. Blood glucose can also be measured by commercially available glucometers that do not require blood or urine samples.

Another aspect of this invention provides methods of lowering blood levels of insulin in a subject by administering the salt and a DPP IV inhibitor. The method comprises administering an effective amount of the salt and DPP IV inhibitor to the mammal. The method further comprises steps to measure blood insulin levels before and after administration of the salt and a DPP IV inhibitor. Blood insulin levels are easily measured by well-known insulin monitoring assays that measure insulin from samples of blood or urine, or as taught herein.

In another aspect, this invention provides methods of increasing blood levels of incretins in a subject by administering the salt and a DPP IV inhibitor. The incretins are GLP-1 and GIP. The method comprises administering an effective amount of the salt and DPP IV inhibitor to the mammal. The method further comprises steps to measure blood incretin levels before and after administration of the salt and a DPP IV inhibitor. Blood incretin levels are easily measured by well-known incretin monitoring assays that, or as taught herein.

Yet another aspect of this invention provides methods of lowering blood triglyceride levels in a subject by administering the salt and a DPP IV inhibitor. The method comprises administering an effective amount of the salt and DPP IV inhibitor to the mammal. The method further comprises steps to measure blood triglycerides levels before and after administration of the salt and DPP IV inhibitor. Blood triglyceride levels are easily measured by numerous commercially available devices that measure blood triglyceride levels from samples of blood.

A further aspect of this invention provides methods of lowering gastric emptying in a subject by administering the salt and a DPP IV inhibitor. The method comprises administering an effective amount of the salt and DPP IV inhibitor to the mammal. The method further comprises steps to measure blood incretin levels before and after administration of the salt and a DPP IV inhibitor. Blood incretin levels are easily measured by well-known incretin monitoring assays, or as taught herein.

Another aspect of this invention provides methods of increasing insulin production in the islet cells of a subject by administering the salt and a DPP IV inhibitor. The method comprises administering an effective amount of the salt and DPP IV inhibitor to the mammal. The method further comprises steps to measure insulin production in islet cells or the beta cells of the pancreas before and after administration of the salt and a DPP IV inhibitor. The insulin production of islets and beta cells are easily measured by well-known assays, or as taught herein.

In yet another aspect, this invention provides methods of preserving islet function in a subject by administering the salt and a DPP IV inhibitor. The method comprises administering an effective amount of the salt and DPP IV inhibitor to the mammal. The method further comprises steps to measure the function of islets' or beta cell's ability to produce insulin before and after administration of the salt and a DPP IV inhibitor. The insulin production of islets and beta cells are easily measured by well-known assays, or as taught herein.

A therapeutically effective amount of the salt and DPP IV inhibitor can be used for the preparation of one or more pharmaceutical compositions useful for treating Type II diabetes and/or lowering the plasma level of glucose. In addition, a therapeutically effective amount of the salt and a DPP IV inhibitor can be used for the preparation of one or more pharmaceutical compositions useful for treating other indications that include diabetes as a component, such as metabolic syndrome, as well as indications that can be improved as a result of increased insulin production (such as the early stages of Type I diabetes).

The compositions of the invention can include the salt and optionally DPP IV inhibitors, pharmaceutically acceptable salts thereof, or a hydrolysable precursor thereof. In general, the salt is mixed with suitable carriers or excipient(s) in a therapeutically effective amount. By a "therapeutically effective dose", "therapeutically effective amount", or, interchangeably, "pharmacologically acceptable dose" or "pharmacologically acceptable amount", it is meant that a sufficient amount of the compound of the present invention and a pharmaceutically acceptable carrier will be present in order to achieve a desired result, e.g., alleviating a symptom or complication of Type II diabetes.

The MBX-2982 salts that are used in the methods of the present invention can be incorporated into a variety of formulations for therapeutic administration. More particularly, the salts can be formulated into pharmaceutical compositions by combination with appropriate, pharmaceutically acceptable carriers, excipients, or diluents, and can be formulated into preparations in solid or semi-solid forms such as tablets, capsules, pills, powders, granules, dragees, gels, ointments, suppositories, inhalants. Administration can be achieved in various ways, including oral, buccal, rectal, intradermal, and transdermal administration. Moreover, the salt can be administered in a local rather than systemic manner, in a depot or sustained release formulation. In addition, the salts can be administered in a liposome.

Suitable formulations for use in the present invention are found in *Remington's Pharmaceutical Sciences* (Mack Publishing Company (1985) Philadelphia, Pa., 17th ed.), which is incorporated herein by reference. The pharmaceutical compositions described herein can be manufactured in a manner that is known to those of skill in the art, i.e., by means of conventional mixing, granulating, dragee-making, levigating, emulsifying, encapsulating, or entrapping processes. The following methods and excipients are merely exemplary and are in no way limiting.

For oral administration, the salt can be formulated readily by combining with pharmaceutically acceptable carriers that are well known in the art. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone. If desired, disintegrating agents can be added, such as the cross-linked polyvinyl pyrrolidone, agar, or alginic acid or the salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the salts according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The salts can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the salts can also be formulated as a depot preparation. Such long acting formulations can be administered by implantation (for example subcutaneously or intramuscularly) or by intramuscular injection. Thus, for example, the salts can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds of the present invention can also be administered by controlled release means and/or delivery devices such as those described in U.S. Pat. Nos. 3,845,770; 3,916,899; 3,536,809; 3,598,123; and 4,008,719.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

The amount of salt that can be combined with a carrier material to produce a single dosage form will vary depending upon the disease treated, the mammalian species, and the particular mode of administration. However, as a general guide, suitable unit doses for the salts can, for example, preferably contain between 0.1 mg to about 1000 mg of the active compound. A preferred unit dose is between 1 mg to about 500 mg. A more preferred unit dose is between 1 mg to about 300 mg. Another preferred unit dose is between 1 mg to about 100 mg. Other preferred unit doses include 25, 50, 100, 150, 200, 250, 300, 350, 400, 450, and 500 mg. The unit does can also be administered 1, 2, 3, 4, 5 or 6 times a day, preferably 1 or 2 times per day, or more preferably once a day so that the total dosage, for example, for a 70 kg adult is in the range of 0.001 to about 15 mg per kg weight of subject per administration. A preferred dosage is about 0.5 to about 10 mg, about 0.5 to about 7.5 mg, about 0.5 to about 5 mg, about 0.5 to about 4 mg, about 0.5 to about 3 mg, about 0.5 to about 2 mg, or about 0.5 to about 1 mg per kg weight of subject per administration, and such therapy can extend for a number of weeks or months, and in some cases, years. It will be understood, however, that the specific dose level for any particular subject will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 500 mg, or a 25, 50, 75, 100, 125, 150, 175, 200, 250, 300, 350, 400, 450, or 500 mg tablet taken once a day or as a time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

In addition, the present invention provides for kits with unit doses of the salt and/or DPP IV inhibitor, either in oral or injectable doses. In addition to the containers containing the unit doses will be an informational package insert describing the use and attendant benefits of the drugs in treating diabetes, obesity, hyperlipidemia, atherosclerosis and metabolic syndrome, and/or their respective related symptoms, complications and disorders.

The following examples are provided to further illustrate certain aspects of the present invention and to aid those of skill in the art in practicing the invention. These examples are not meant to limit the scope of the invention.

EXAMPLES

The following abbreviations are used in the Examples and throughout the application.

| ACN | Acetonitrile |
|---|---|
| DCM | Dichloromethane |
| DEE | Diethyl ether |
| EtOAc | Ethyl acetate |
| EtOH | Ethanol |
| HFIP | Hexafluoroisopropanol |
| IPA | Isopropyl alcohol |
| IPE | Isopropyl ether |
| MEK | Methyl ethyl ketone |
| MeOH | Methanol |
| MTBE | Methyl-tert-butyl ether |
| TFE | 2,2,2-Trifluoroethanol |
| THF | Tetrahydrofuran |
| CCS | Crash cooling of a solution |
| FC | Fast cooling |
| FE | Fast evaporation |
| RE | Rotary evaporation |
| S/AS | Solvent/Anti-solvent precipitation |
| SC | Slow cooling |
| SE | Slow evaporation |
| VD | Vapor diffusion |
| VO | Vacuum Oven |
| DSC | Differential scanning calorimetry |
| NMR | Nuclear magnetic resonance spectroscopy |
| TG/TGA | Thermogravimetric analysis |
| XRPD | X-ray powder diffraction |
| B/E | Birefringence/extinction |
| NS | No solids |
| Ppt | Precipitation |
| RH | Relative humidity |
| RT | Room temperature |

Instrumental Techniques

XRPD: XRPD patterns were collected using an Inel XRG-3000 diffractometer or PANalytical X'Pert Pro diffractometer.

Inel: Inel XRG-3000 diffractometer equipped with a curved position sensitive detector with a 2θ range of 120°. An incident beam of Cu Kα radiation (40 kV, 30 mA) was used to collect data in real time at a resolution of 0.03° 2θ. Prior to the analysis, a silicon standard (NIST SRM 640c) was analyzed to verify the Si 111 peak position. Samples were prepared for analysis by packing them into thin-walled glass capillaries. Each capillary was mounted onto a goniometer head and rotated during data acquisition.

PANalytical: An incident beam of Cu Kα radiation was produced using an Optix long, fine-focus source. An elliptically graded multilayer mirror was used to focus the Cu Kα X-rays of the source through the specimen and onto the detector. Data were collected and analysed using X'Pert Pro Data Collector software (v. 2.2b). Prior to the analysis, a silicon specimen (NIST SRM 640c) was analyzed to verify the Si 111 peak position. The specimen was sandwiched between 3 μm thick films, analyzed in transmission geometry, and rotated to optimize orientation statistics. Soller slits were used for the incident and diffracted beams to minimize axial divergence. Diffraction patterns were collected using a scanning position-sensitive detector (X'Celerator) located 240 mm from the specimen.

DSC: DSC was performed using a TA Instruments Q2000 differential scanning calorimeter. Temperature calibration was performed using NIST traceable indium metal. The sample was placed into an aluminum DSC pan, and the weight was accurately recorded. The pan was either covered with a lid perforated with a laser pinhole, and the lid was hermetically sealed or covered with an unperforated lid and crimped. The sample cell was equilibrated at either −30° C. or 25° C. and heated under a nitrogen purge at a rate of 10° C./minute, up to a final temperature of 250° C. Reported temperatures are at the transition maxima.

TGA: TG analyses were performed using a TA Instruments Q5000 IR thermogravimetric analyzer. Temperature calibration was performed using nickel and Alumel™. Each sample was placed in an aluminum pan. The pan was hermetically sealed with a lid that was opened using a punching mechanism just before being inserted into the TG furnace. The furnace was heated under nitrogen at a rate of 10° C./minute to a final temperature of 350° C.

$^1$H NMR: The solution NMR spectra were acquired with a Varian $^{UNITY}$INOVA-400 spectrometer. The samples were prepared by dissolving them in CDCl$_3$ or in DMSO$_6$.

FT-Raman spectroscopy: Raman spectra were acquired on a Nexus 670 FT-Raman accessory module interfaced to a Nexus 670 FT-IR spectrophotometer (Thermo Nicolet) equipped with an indium gallium arsenide (InGaAs) detector. Wavelength verification was performed using sulfur and cyclohexane. Each sample was prepared for analysis by placing the sample into a glass tube and positioning the tube in a gold-coated tube holder.

Crystallization Methods

Slow Cool (SC): Solutions containing free base and an acid of interest were prepared in various solvents at room temperature. Solids persisted and, the samples were heated to facilitate dissolution. Once a clear (solids-free) solution was obtained, the solutions were allowed to slowly cool to room temperature.

Volume Reduction (VR): Solutions containing free base and an acid of interest were prepared in various solvents at room temperature. No solids were seen in solution. Sample capped and left at ambient temperature for a period of hours to days. If no solids were generated, the sample was uncapped and the samples volume was reduced. Sample capped and allowed to stand under ambient temperature conditions. Once solids precipitated from solution, the solids were collected via vacuum filtration and dried.

Precipitation (Ppt): Solutions containing free base and an acid of interest were prepared in various solvents at room temperature. If solids persisted, the samples were either heated to facilitate dissolution or kept at ambient temperature and stirred. If a clear solution resulted, the sample was capped and kept at ambient temperature. The samples at elevated temperature were cooled to ambient temperature. Generated solids were collected via vacuum filtration and dried.

Example 1

Preparation free base 5-ethyl-2-{4-[4-(4-tetrazol-1-yl-phenoxymethyl)-thiazol-2-yl]-piperidin-1-yl}-pyrimidine Synthesis of tert-butyl 4-(4-((4-(1H-tetrazol-1-yl)phenoxy)methyl)thiazol-2-yl)piperidine-1-carboxylate A mixture of 4-(4-chloromethyl-thiazol-2-yl)-piperidine-1-carboxylic acid tert-butyl ester (549 mg), 4-tetrazol-1-ylphenol (270 mg), $Cs_2CO_3$ (890 mg) in acetonitrile was heated under reflux overnight. After cooling, the reaction mixture was filtered through a pad of celite, concentrated in vacuo. Purification by chromatography (40-100% EtOAc/Hexanes) gave the desired product as a white solid. $^1$H NMR (CDCl$_3$): δ 8.01 (1H, s), 7.61 (2H, d, J=8.8 Hz), 7.25 (1H, s), 7.15 (2H, d, J=8.8 Hz), 5.22 (2H, s), 4.2 (2H, br), 3.17 (1H, m), 2.87 (2H, m), 2.11 (2H, m), 1.73 (2H, m), 1.46 (9H, s).

Synthesis of 4-[4-(4-tetrazol-1-yl-phenoxymethyl)-thiazol-2-yl]-piperidine hydrochloride To a solution of tert-butyl 4-(4-((4-(1H-tetrazol-1-yl)phenoxy)methyl)thiazol-2-yl)piperidine-1-carboxylate (0.60 g) in methanol/dichloromethane (1.0 mL/1.5 mL) was added 4N HCl in dioxane (1.7 mL) at 0° C., and then stirred at room temperature for 7 hours. After removal of solvents in vacuo, a crude desired compound HCl salt was obtained as an off-white solid.

A mixture of 4-[4-(4-tetrazol-1-yl-phenoxymethyl)-thiazol-2-yl]-piperidine hydrochloride (403 mg), 2-chloro-5-ethylpyrimidine (0.15 mL) and diisopropylethylamine (1 mL) in isopropanol was heated at 90° C. overnight, partitioned between EtOAc and water. The organic layer was washed with water/brine, and dried over anhydrous $Na_2SO_4$ and concentrated in vacuo. Purification by chromatography on silica gel (40-100% EtOAc/hexanes) gave the desired compound as a white solid. $^1$H NMR (DMSO-d$_6$): δ 9.98 (1H, s), 8.24 (2H, s), 7.80 (2H, d, J=8.8 Hz), 7.66 (1H, s), 7.28 (2H, d, J=8.8 Hz), 5.20 (2H, s), 4.67 (2H, m), 3.32 (1H, m), 3.01 (2H, m), 2.43 (2H, q, J=7.2 Hz), 2.07 (2H, m), 1.59 (2H, m), 1.11 (3H, t, J=7.2 Hz) ppm.

Example 2

Besylate Salt

The besylate salt was generated from an acetone solution volume reduction experiment. The material crystallized as stacked plates. XRPD analysis indicated the besylate salt was crystalline. After overnight RH stress, the material remained a free-flowing powder. Thermal analysis of the stressed sample indicated a slight weight loss (0.9 wt. %) to 125° C. and a sharp endotherm centered at 153° C. Associated with the endotherm was a shoulder at approximately 147° C. Rapid weight loss was observed above approximately 155° C. $^1$H NMR spectroscopy results indicated a 1:1 salt was present.

$^1$H NMR (CDCl$_3$): δ 8.95 (1H, s), 8.54 (2H, br s), 7.95 (2H, m), 7.63 (2H, dt, J=3, 9.2 Hz), 7.40 (3H, m), 7.29 (1H, s), 7.18 (2H, dt, J=3, 9.2), 5.24 (2H, s), 4.76 (2H, m), 3.42 (3H, m), 2.61 (2H, q, J=7.6 Hz), 2.33 (2H, dd, J=3, 13.8 Hz), 1.97 (2H, m), 1.26 (3H, t, J=7.6 Hz).

Example 3

Camsylate Salt

The camsylate salt was generated by a precipitation reaction and a slow cool in acetone. The material crystallized in an unknown morphology. XRPD analysis indicated the camsylate salt was crystalline. After overnight RH stress, the material remained a free flowing powder. Thermal analysis of the unstressed material indicated a slight weight loss (0.3 wt. %) to 125° C. and a sharp endotherm centered at 184° C. Rapid weight loss, usually indicative of decomposition, was observed above approximately 180° C. $^1$H NMR spectroscopy results indicated that a 1:1 salt had formed.

$^1$H NMR (CDCl$_3$): δ 8.70 (1H, s), 8.61 (2H, br s), 7.74 (2H, d, J=9.2 Hz), 7.28 (1H, s), 7.18 (2H, d, J=9.2 Hz), 5.24 (2H, s), 4.78 (2H, d, J=13.6 Hz), 3.42 (4H, m), 2.92 (1H, d, J=15.2 Hz), 2.73 (1H, m), 2.62 (2H, q, J=7.6 Hz), 2.34 (3H, m), 1.99 (4H, m), 1.89 (1H, d, J=18.4 Hz), 1.79 (1H, m), 1.39 (1H, m), 1.27 (3H, t, J=7.6 Hz), 1.12 (3H, s), 0.86 (3H, s).

Example 4

Esylate Salt

The esylate salt was generated through a precipitation reaction in acetone. The esylate material existed as stacked plates and tablets. XRPD analyses indicated that the esylate salt was crystalline. After overnight stress, the material remained a free flowing powder. Thermal analysis of the stressed powder indicated a 4.8% weight loss to 125° C. and a sharp endotherm centered at 98.5° C. The endothermic event is typically indicative of a melting event. The weight loss could be indicative of a solvate or hydrate of the salt. Rapid weight loss, usually indicative of decomposition, was observed above approximately 125° C. $^1$H NMR spectroscopy results indicated a 1:1 salt had formed.

$^1$H NMR (CDCl$_3$): δ 8.95 (1H, s), 8.56 (2H, br s), 7.63 (2H, d, J=9.2 Hz), 7.29 (1H, s), 7.18 (2H, d, J=9.2 Hz), 5.24 (2H, s), 4.79 (2H, m), 3.43 (3H, m), 2.97 (2H, q, J=7.6 Hz), 2.61 (2H, q, J=7.6 Hz), 2.36 (2H, m), 1.98 (2H, m), 1.39 (3H, t, J=7.6 Hz), 1.27 (3H, t, J=7.6 Hz).

Example 5

HBr Salt

The HBr salt was generated through a precipitation reaction in acetone. The material crystallized in an unknown morphology. XRPD results indicated that the HBr salt was crystalline. After overnight stress, the material remained a free flowing powder. Thermal analysis of the unstressed material indicated that a wide, weak endotherm existed prior to the sample undergoing decomposition. A 1.5% wt. loss was detected prior to decomposition. $^1$H NMR spectroscopy indicated that no decomposition product was formed under ambient conditions. The salt precipitated in the presence of CDCl$_3$ and the $^1$H NMR analysis was performed in DMSO.

$^1$H NMR (DMSO-d$_6$): δ10.00 (1H, s), 8.30 (2H, s), 7.82 (2H, d, J=9.2 Hz), 7.68 (1H, s), 7.30 (2H, d, J=9.2 Hz), 5.22 (2H, s), 4.66 (2H, d, J=13.2 Hz), 3.36 (1H, tt, J=3.8, 11.6 Hz), 3.08 (2H, dt, J=2.6, 12.8 Hz), 2.50 (2H, q, J=7.4 Hz), 2.12 (2H, m), 1.64 (2H, m), 1.14 (3H, t, J=7.4 Hz).

Example 6

Mesylate Salt

The mesylate salt was generated in a variety of morphologies using a slow cool/volume reduction technique. XRPD results indicated that the mono-salt was crystalline. After elevated RH stress, the material remained a free flowing powder. Thermal analysis of the post-stress sample indicated an endotherm centered at 86° C. and a weight loss of 4.5% up to 125° C. One possible explanation is that solvent (probably water) loss occurs quickly and the sample undergoes decomposition after a melting event. $^1$H NMR spectroscopy results confirmed a 1:1 salt was formed.

$^1$H NMR (CDCl$_3$): δ 8.95 (1H, s), 8.55 (2H, br s), 7.63 (2H, d, J=8.8 Hz), 7.29 (1H, s), 7.18 (2H, d, J=9.2 Hz), 5.24 (2H, s), 4.76 (2H, m), 3.42 (3H, m), 2.88 (1H, s), 2.61 (2H, q, J=7.6 Hz), 2.36 (2H, m), 1.99 (2H, m), 1.27 (3H, t, J=7.6 Hz).

XRPD (Intel XRG-3000 diffractometer) select interlattice plane intervals: d in [Å] (±0.1 Å): 10.23, 6.28, 4.83, 4.75, 4.57, 4.43, 4.32, 3.49, 3.43, 3.32.

Example 7

Sulfate Salt

The sulfate salt was generated from precipitation experiments. XRPD results indicated that the mono-salt generated crystalline material. After elevated RH stress, the material turned tacky. Thermal analysis of the unstressed sample indicated a large weight loss (9% to 125° C.) was associated with an endotherm centered at 97° C. After this initial weight loss, rapid degradation of the material occurred upon further heating which may be due the loss of water, although this hypothesis was not verified. $^1$H NMR spectroscopy results indicated that no decomposition product was formed. The salt precipitated in the presence of CDCl$_3$ and the $^1$H NMR analysis was performed in DMSO.

$^1$H NMR (DMSO-d$_6$): δ10.00 (1H, s), 8.32 (2H, s), 7.82 (2H, d, J=9.2 Hz), 7.68 (1H, s), 7.30 (2H, d, J=9.2 Hz), 5.22 (2H, s), 4.65 (2H, d, J=13.6 Hz), 3.36 (1H, tt, J=3.6, 11.2 Hz), 3.09 (2H, m), 2.48 (2H, q, J=7.6 Hz), 2.12 (2H, m), 1.65 (2H, m), 1.14 (3H, t, J=7.6 Hz).

Example 8

Tosylate Salt

The tosylate salt was generated by slow cooling and volume reduction in acetone. The material crystallized in an unknown morphology. XRPD results indicated that crystalline material existed. The material remained a free flowing powder after exposure to elevated RH conditions. Thermal analysis of the material indicated minor (0.9%) weight loss to 125° C. associated with a very weak endotherm centered at 94° C. This wide, weak endotherm could be indicative of solvent loss. An endotherm centered at 152° C. preceded a large loss in weight. $^1$H NMR spectroscopy results confirmed a 1:1 salt had formed.

$^1$H NMR (CDCl$_3$): δ 8.95 (1H, s), 8.54 (2H, br s), 7.83 (2H, d, J=8.0 Hz), 7.63 (2H, d, J=9.2 Hz), 7.30 (1H, s), 7.19 (4H, m), 5.25 (2H, s), 4.76 (2H, m), 3.43 (3H, m), 2.61 (2H, q, J=7.6 Hz), 2.36 (3H, s), 2.33 (2H, m), 1.96 (2H, m), 1.26 (3H, t, J=7.6 Hz).

XRPD (Intel XRG-3000 diffractometer) select interlattice plane intervals: d in [Å] (±0.1 Å): 10.61, 8.41, 5.78, 5.17, 5.02, 4.84, 4.37, 4.22, 3.95, 3.44.

Example 9

HCl Salt

A screen of various solvent systems for preparing the HCl salts was undertaken according to the following procedures, with the results shown in Table 6 below.

Evaporation Experiments: HCl salt was dissolved in a given solvent. The solution was filtered through a 0.2 μm nylon filter. For evaporation experiments at ambient, the solutions were left in open vials (fast evaporation) or covered with aluminum foil containing pinholes (slow evaporation). For evaporation experiments under vacuum (rotary evaporation), the sample was placed on the rotary evaporator at ambient or elevated temperature and the solvents evaporated to dryness.

Slow and Fast Cool Experiments: HCl salt was contacted with a given solvent and the sample was brought to elevated temperature in an oil bath on a hotplate. Selected samples were filtered using a 0.2 μm nylon filter. The heat source was then turned off and the hotplate and vials were allowed to cool slowly in the oil bath to ambient temperature for slow cool or placed on the lab bench for fast cool. Selected samples that did not produce solids at ambient temperature were placed in a refrigerator or freezer. Solids were recovered by vacuum filtration.

Crash Cool Experiments: Saturated solutions were prepared in various solvents at elevated temperature. Experiments were performed in an oil bath placed on a hotplate. The resulting solutions or slurries were rapidly filtered through a warm 0.2 μm filter into an open vial while still warm. The vial was placed into an acetone bath cooled by dry ice. Solids were collected by vacuum filtration.

Vapor Diffusion: Small amounts of MBX 2982HCl were dissolved in a minimum amount of an appropriate solvent. The samples were filtered through a 0.2 μm nylon filter into a 1 dram vial. Diethyl ether was added to a 20 mL scintillation vial. The 1 dram vials were uncapped and placed into the 20 mL vials. The 20 mL vials were capped and parafilmed.

TABLE 6

| Solvent | Conditions | Observation | XRPD Results |
|---|---|---|---|
| Acetone:MeOH (~3:1) | FC from ~53° C. to RT (cloudy), sonicated, left standing, ~3 days | Needle-like, agglomerates, some B/E on small particles | Form II |
| Chloroform | SC from ~53° C. to RT (clear), sonicated, left standing, ~3 days | NS | |
| DCM | FE | Unknown morphology, agglomerates, B/E | Pattern E |
| DCM | Agitation w/stirring, RT, ~3 days$^a$ | Unknown morphology, agglomerates, no B/E | Form I |
| DCM/DEE | VD | Fibrous or needle-like, agglomerates, some B/E | Pattern C |
| EtOH:water (2:1) | Slurry w/stirring, RT, ~1 day | Unknown morphology, agglomerates, some B/E on very small particles | Form I + free base Form II |
| IPA | Slurry, ~60° C., ~3 days | Unknown morphology to granule-like, some B/E | Form I |

TABLE 6-continued

| Solvent | Conditions | Observation | XRPD Results |
|---|---|---|---|
| MeOH | SE | Unknown morphology, agglomerates, some B/E on smaller particles | Form I |
| MeOH | Slurry w/stirring, RT, ~3 days | Unknown morphology, agglomerates, no B/E | Form I |
| MeOH | CCS (acetone/dry ice) from ~58° C. | Unknown morphology, agglomerates, some B/E on small particles | Form I + II |
| MeOH/ACN | S/AS attempt (clear). Kept in freezer | NS | |
| MeOH/DEE | VD | Fibrous + needle-like, + opaque, agglomerates some B/E | Pattern L |
| MeOH:EtOAc (1:1) | SC from ~57° C. to RT | Rosettes to needle-like, agglomerates, B/E | Form II |
| MeOH:THF (1:1) | Slurry, RT, ~5 days | Unknown morphology, agglomerates, B/E on few small particles | Form I |
| MeOH:EtOAc (1:1) | Slurry, ~40° C., ~2 days | Unknown morphology, agglomerates, some B/E on few particles | Form I |
| Nitromethane | Slurry, ~60° C., ~3 days | Unknown morphology, agglomerates, some B/E on smaller particles | Form I |
| Nitromethane | SC from ~69° C. to RT (clear), sonicated, kept in refrigerator, 4 days | Unknown to needle-like particles, agglomerates, some B/E on smaller particles | Pattern J |
| TFE | RE, RT to ~40° C. (film) | Unknown morphology, generally opaque, some B/E on very small particles | Pattern H |
| TFE:ACN (19:1) | Slurry, ~40° C., ~2 days | Unknown morphology to granule-like, agglomerates, some B/E on smaller particles | Form I |
| TFE/DEE | VD | Unknown morphology, agglomerates, some B/E on smaller particles | Form I |
| TFE/EtOAc | S/AS attempt (clear). Kept in freezer | Unknown morphology to rosettes, agglomerates, some B/E on smaller particles | Pattern G |
| THF:TFE (1:1) | SC from ~53° C. to RT (clear), sonicated, kept in freezer, ~4 days | Unknown morphology, agglomerates, some B/E on smaller particles | Pattern K |
| Water | Slurry, ~38° C., ~1 day | Unknown morphology, agglomerates, some B/E on small particles | Pattern D |

Example 10

HCl salt Form I

The free base (46.0 g) contacted with 500 mL EtOH and warmed/stirred. 9.5 mL conc. HCl added to the suspension. Sample was left for approximately 30 minutes and then cooled to RT. The filtered material was vacuum dried (3 days) and identified as "pattern O" containing trace amounts of ethanol.

$^1$H NMR (CDCl$_3$): δ 8.95 (1H, s), 8.42 (2H, br s), 7.63 (2H, d, J=9.2 Hz), 7.28 (1H, s), 7.18 (2H, d, J=9.2 Hz), 5.24 (2H, s), 4.97 (2H, m), 3.46 (3H, m), 2.61 (2H, q, J=7.6 Hz), 2.37 (2H, m), 1.99 (2H, m), 1.27 (3H, t, J=7.6 Hz).

The solids were re-combined with original mother liquor and sample was rapidly stirred and an additional 0.5 mL conc. HCl added. Sample was heated and stirred for approximately 30 minutes and then allowed to slowly cool to RT. The filtered material was slurried in acetone (26.8 g/125 mL) and warmed for approximately one (1) hour. The sample was slowly cooled to ambient temperature and slurried for six days to give HCl Form I.

The results of thermal (DSC, TGA) characterization of HCl Form I indicated that the material is likely unsolvated. The TGA curve indicates a ~0.2% weight loss between ~23° C. and ~73° C., likely associated with residual acetone evaporation (presence of residual acetone is seen from $^1$H NMR). A weight loss of approximately 13.1% between ~113° C. and ~210° C. was observed, followed by a sharp loss at ~302° C. (onset) likely due to decomposition. The material may initially lose the HCl, which is accompanied by further degradation at higher temperatures. The DSC thermogram exhibited a sharp endothermic event at ~191° C. (onset) followed by immediate heat fluctuation, likely attributable to decomposition.

Moisture sorption results showed a ~0.3 wt % loss upon equilibration at ~5% RH. The small weight loss is comparable with the TGA loss, and is likely associated with the loss of residual acetone. A steady ~0.9 wt % gain was observed between ~5% and ~95% RH. A complete desorption occurred upon decreasing relative humidity to ~5% (~0.9 wt % loss between ~95% and ~5% RH).

The $^1$H NMR showed significant shift and broadening of peak at 8.42 ppm attributable to protons of pyrimidine ring and traces of residual acetone (~0.06 moles of acetone per mole of free base).

$^1$H NMR (CDCl$_3$): δ 8.96 (1H, s), 8.42 (2H, br s), 7.63 (2H, d, J=8.8 Hz), 7.28 (1H, s), 7.18 (2H, d, J=8.8 Hz), 5.24 (2H, s), 4.98 (2H, m), 3.45 (3H, m), 2.61 (2H, q, J=7.6 Hz), 2.38 (2H, m), 1.99 (2H, m), 1.27 (3H, t, J=7.6 Hz).

The elemental analysis data was consistent with the material being a monohydrochloride salt: (C$_{22}$H$_{25}$ClN$_8$OS) C: 54.16%; H: 5.29%; N: 22.89%; Cl: 7.40%.

FT-Raman spectrum: (cm$^{-1}$): 154, 193, 214, 243, 324, 346, 384, 420, 460, 467, 495, 539, 573, 596, 628, 648, 680, 687, 718, 751, 766, 787, 800, 845, 856, 946, 967, 992, 1009, 1051, 1068, 1094, 1110, 1172, 1203, 1225, 1253, 1282, 1300, 1311, 1334, 1375, 1394, 1404, 1432, 1458, 1474, 1480, 1517, 1533, 1591, 1609, 1637, 2734, 2869, 2903, 2928, 2937, 2967, 2999, 3015, 3030, 3063, 3075.

Example 11

HCl Salt Form I from Acetone

To a suspension of MBX-2982 (0.9 g) in acetone (4 mL) was added one equivalent of HCl (concentrated aqueous solution) at 55° C. The suspension was stirred at 55° C. for two hours and then cooled down to room temperature. The HCl salt Form I was collected by vacuum filtration as solids. Select interlattice plane intervals from the X-ray powder pattern taken from an Intel XRG-3000 diffractometer: d in [Å] (±0.1 Å): 10.09, 8.20, 5.51, 5.08, 4.36, 4.26, 4.14, 4.08, 3.35, 3.18.

Example 12

HCl Salt Form I from Ethyl Acetate

To a suspension of MBX-2982 (2 g) in ethyl acetate (9 mL) was added 1.05 equivalent of HCl (1 M solution in ethyl acetate) at 55° C. The suspension was stirred at 55° C. for two hours and then cooled down to room temperature. The HCl salt Form I was collected by vacuum filtration as solids. Select interlattice plane intervals from the X-ray powder pattern taken from an Intel XRG-3000 diffractometer: d in [Å] (±0.1 Å): 10.09, 8.22, 5.51, 5.09, 4.36, 4.26, 4.14, 4.09, 3.35, 3.18.

Example 13

HCl Salt Form II 21.5 g pattern O material (prepared as in Example 10) was contacted with 125 mL MeOH and HCl Form II seeds. Sample was slurried for 6 days at RT to give Form II material.

XRPD analysis of HCl Form II shows that the material is crystalline.

$^1$H NMR analysis of HCl Form II indicated significant shift and broadening of the peak at ~8.42 ppm, attributable to protons in the pyrimidine ring, and suggest that HCl is likely positioned near the pyrimidine nitrogen atoms. In addition, the spectrum also showed traces of methanol (0.3 moles of methanol per mole of base) and residual ethyl acetate.

$^1$H NMR (CDCl$_3$): δ 8.98 (1H, s), 8.42 (2H, br s), 7.63 (2H, d, J=8.8 Hz), 7.29 (1H, s), 7.18 (2H, d, J=9.2 Hz), 5.24 (2H, s), 4.98 (2H, m), 3.47 (3H, m), 2.61 (2H, q, J=7.6 Hz), 2.37 (2H, m), 1.99 (2H, m), 1.27 (3H, t, J=7.6 Hz).

The results of thermal (DSC, TGA) characterization of Form II suggest that the material is likely unsolvated. The TG curve indicates a ~0.6% weight loss between ~21° C. and ~113° C., likely associated with residual methanol and ethyl acetate evaporation. A weight loss of approximately 14.6% between ~113° C. and ~220° C. was observed, followed by a sharp loss at ~312° C. (onset) likely due to decomposition. The material may initially lose the HCl, which is accompanied by further degradation at higher temperatures. The DSC thermogram exhibited an endothermic event beginning ~150° C. (onset) followed by a number of heat fluctuations, likely attributable to decomposition.

Biological Example 1

Two studies were conducted in order to compare the systemic exposure and pharmacokinetics (PK) of microcrystalline MBX-2982 and salt forms of MBX-2982 in fasted male Sprague Dawley (SD) rats following single oral gavage (PO) doses of 200 mg/kg. Four salt forms of MBX-2982 were investigate in the studies. The tested salts were HCl Form I, HCl salt Form II, mesylate salt and the tosylate salt.

Materials and Equipment
Standard: MBX-2982
Internal standard: MBX-2982, where the six phenyl ring carbon atoms are labeled as $^{13}$C
Blank pooled rat plasma (Bioreclamation)
Chemicals: Reagent grade
Solvents: HPLC grade
96-well deep plate and mat: 1 mL (Corning)
HPLC Column: Lunar C18 (2), 5μ, 50×2.1 mm I.D. (Phenomenex)
Pre-column filter: 0.2 μm (Thermo-Fisher Scientific)
LC System: LC-20 AD Pumps and SCL-10A VP LC controller with CTC Analytics AG Pal Autosampler (Shimadzu Scientific Instruments, Inc.)
Mass Spectrometer: 4000 Q-TRAP® with Analyst 1.4.2 Software (Applied Biosystem Inc.)
Analytical balance: model accu-124 (Fisher Scientific)
Pipets: (Rainin Instrument, LLC)

Sample Preparation

Preparation of samples was performed by solvent precipitation of plasma proteins in a 1 mL/well 96-well plate. Standards were prepared by spiking 10 μL of blank plasma with 10 μL of standard solution (acetonitrile containing MBX-2982 at 0.01, 0.02, 0.05, 0.1, 0.2, 0.5, 1, 2, 5, 10, 20, 50 and 100 μg/mL) and 300 μL of 0.1% formic acid in acetonitrile containing 0.2 μg/mL internal standard. Plasma samples were prepared by adding 10 μL of plasma sample, 10 μL of acetonitrile, and 300 μL of 0.2 μg/mL internal standard in 0.1% formic acid in acetonitrile. After addition of the organic solvents, all samples were vortexed briefly and centrifuged at 3600 rpm for 10 minutes. Some of the samples were diluted 1.3 to 2-fold with blank plasma. An aliquot of the supernatant (25 μL) was transfer to a 1 mL/well 96-well plate and mixed with 200 μL water/ACN (50/50, v/v) and injected into the HPLC.

All stock and spiking solutions were kept in polypropylene tubes and stored at approximately −80° C.

The suspensions for microcrystalline MBX-2982 (free base) and salt forms of MBX-2982 were prepared in 1% carboxymethylcellulose and 2% tween 80 in water (w/w/v).

Five groups of animals were given microcrystalline and salt forms suspension doses of MBX-2982 orally at 200 mg/kg, respectively. Food was withheld the night before dose and returned nine hours after dosing. Blood samples were collected at 0.25, 0.5, 1, 2, 4, 6, 9, 24, 30 and 48 h post dose. MBX-2982 plasma concentration from these samples was analyzed by a non-validated high performance liquid chromatography in conjunction with mass spectrometry (LC-MS/MS) method.

Plasma concentration-time data for individual animals were analyzed using WinNonlin software (Professional, version 5.0.1; Pharsight Corp.). A non-compartmental model (model 200) was used. Peak area ratios of MBX-2982 to internal standard and concentration were fitted to a quadratic equation (Calibration Curve) with 1/x weighting using a quadratic regression program in Analyst version 1.4.2 (Applied Biosystem Inc). The equations were then used to interpolate the concentrations of MBX-2982 in samples from peak area to internal standard ratio.

Figure 23:
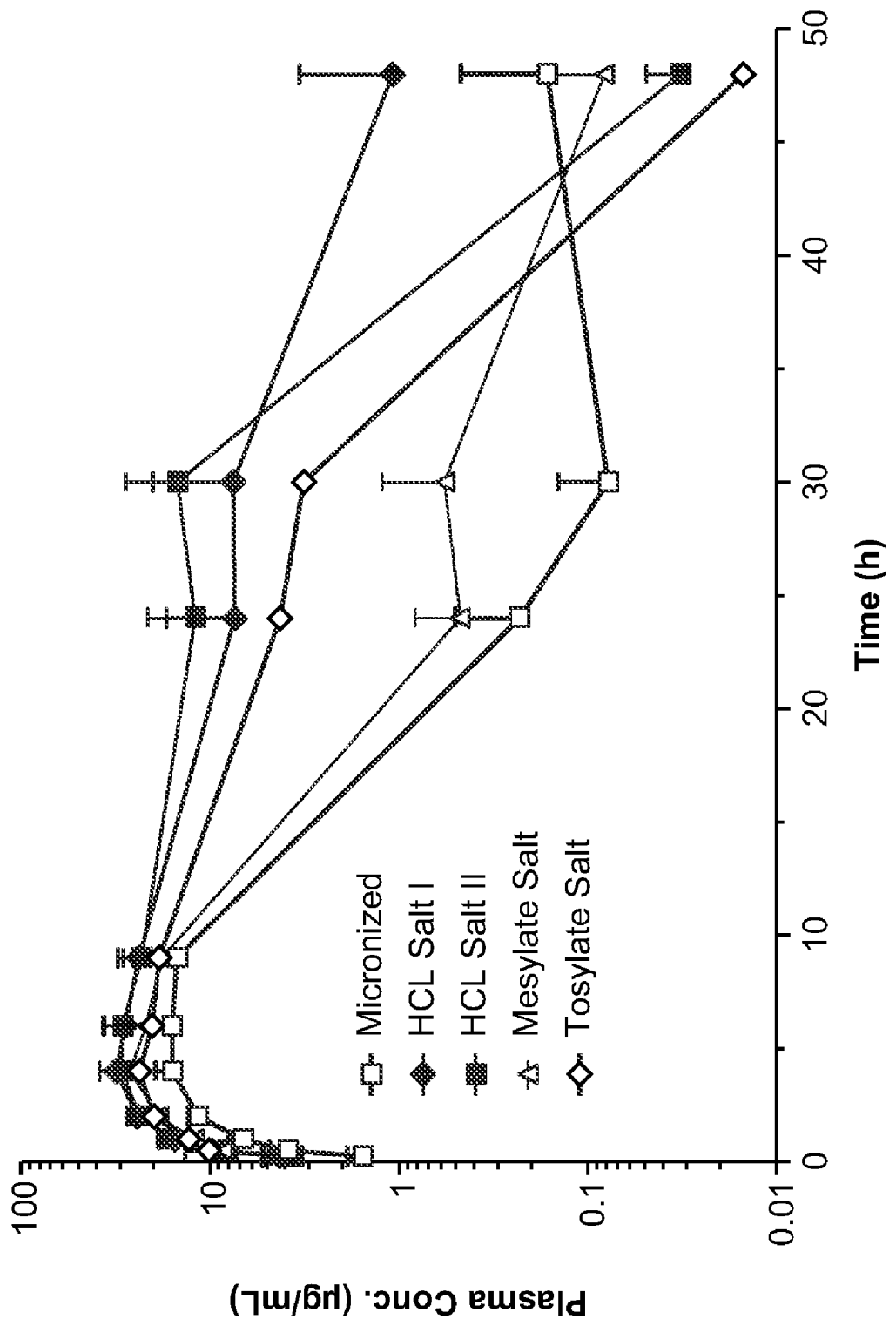
FIG. 23 shows the mean plasma concentrations of micronized MBX-2982 free-base, HCl Forms I and II, and the mesylate and tosylate salts versus time in male SD rats following single oral dose of 200 mg/kg.

The following pharmacokinetic parameters were calculated:
1) $C_{max}$: Maximum (peak) plasma concentration
2) $T_{max}$: Time at which $C_{max}$ occurred
3) $t_{1/2}$: Terminal phase half-life
4) $AUC_{0-t}$: Area under the concentration-time curve from time 0 to last measurable concentration
5) $AUC_{0-inf}$: Area under the concentration-time curve from time 0 extrapolated to infinity The mean pharmacokinetic parameters of MBX-2982 in male SD rats following single 200 mg/kg PO doses are presented in Table 7. Mean plasma concentration-time data and profiles are presented in Table 8 and FIG. 23.

The results show that the tested salt forms of MBX-2982 gave higher drug exposure compared with micro MBX-2982 (free base) when dosed with equivalent amounts. The systemic drug exposures in $AUC_{0-t}$ increased 2.4-fold, 2.9-fold, 1.4-fold and 1.7 fold for HCl salt Form I, HCl form II, mesylate salt and tosylate salt, respectively.

TABLE 7

Mean pharmacokinetic parameters (Mean ± SD) of MBX-2982 in Fasted male SD rats following single PO dose of 200 mg/kg

| Parameter | MBX-2982 | HCl Salt Form I | HCl Salt Form II | Mesylate Salt | Tosylate Salt |
|---|---|---|---|---|---|
| $t_{1/2}$ (h) | 3.53 ± 0.70 | 4.01 ± 1.68 | 2.09 ± | 4.11 ± 1.29 | 3.20 ± 0.88 |
| $T_{max}$ (h) | 5.88 ± 1.55 | 7.25 ± 9.25 | 11.5 ± 12.4 | 4.50 ± 1.00 | 4.00 ± 1.63 |
| $C_{max}$ (μg/mL) | 17.4 ± 4.19 | 31.2 ± 7.41 | 31.8 ± 5.05 | 26.7 ± 4.46 | 26.1 ± 7.98 |
| $AUC_{0-24}$ (μg * h/mL) | 233 ± 64.8 | 454 ± 98.4 | 482 ± 69.4 | 314 ± 65.7 | 342 ± 117 |
| $AUC_{0-t}$ (μg * h/mL) | 236 ± 64.6 | 571 ± 249 | 679 ± 208 | 322 ± 63.6 | 392 ± 98.2 |
| $AUC_{0-inf}$ (μg * h/mL) | 1.89 ± 60.7 | 536 ± 29.9 | 469 ± | 323 ± 62.0 | 393 ± 98.1 |

TABLE 8

Mean concentrations (μg/mL; mean ± SD) at the indicated time points of MBX-2982 in Fasted male SD rats following single PO dose of 200 mg/kg

| Time (h) | MBX-2982 | HCl Salt Form I | HCl Salt Form II | Mesylate Salt | Tosylate Salt |
|---|---|---|---|---|---|
| 0.5 | 3.89 ± 0.95 | 9.79 ± 3.73 | 8.06 ± 1.61 | 8.52 ± 0.975 | 10.1 ± 2.45 |
| 1 | 6.70 ± 1.27 | 15.5 ± 3.15 | 16.3 ± 2.77 | 12.2 ± 0.839 | 13.0 ± 3.33 |
| 2 | 11.6 ± 1.61 | 24.2 ± 3.35 | 23.7 ± 4.22 | 18.8 ± 0.904 | 19.7 ± 2.55 |
| 4 | 15.8 ± 3.74 | 31.4 ± 7.10 | 29.2 ± 3.71 | 26.7 ± 4.39 | 23.6 ± 6.90 |
| 6 | 15.9 ± 4.94 | 28.1 ± 8.46 | 29.1 ± 8.13 | 21.8 ± 6.48 | 20.3 ± 11.2 |
| 9 | 15.0 ± 5.90 | 23.8 ± 6.99 | 23.2 ± 5.70 | 18.0 ± 5.18 | 18.6 ± 10.55 |
| 24 | 0.26 ± 0.28 | 7.43 ± 9.63 | 12.02 ± 9.33 | 0.476 ± 0.344 | 4.2 ± 5.51 |
| 30 | 0.08 ± 0.06 | 7.52 ± 12.63 | 14.9 ± 13.2 | 0.574 ± 0.641 | 3.18 ± 5.88 |
| 48 | 0.16 ± 0.30 | 1.08 ± 2.31 | 0.0325 ± | 0.082 ± 0.082 | 0.02 ± 0.01 |

In the treatment of diabetes, it is advantageous to maintain effective concentrations of drug in the blood over periods of time that permit once a day dosing. As shown in Table 8 and FIG. 23, at 24 hours post-dosing, the plasma level of micronized, free-base MBX-2982 was 0.26 μg/ml. In contrast, at 24 hours, the plasma levels of the salt forms were 7.3 μg/ml (HCl form I), 12.02 μg/ml (HCl form II), 0.476 μg/ml (mesylate), and 4.2 μg/ml (tosylate). At 30 hours post-dose, the plasma levels of the micronized, free-base MBX-2982 was 0.08 μg/ml, and the salt forms were 7.52 μg/l (HCl form I), 14.9 μg/ml (HCl form II), 0.574 μg/ml (mesylate), and 3.18 μg/ml (tosylate). Thus at 30 hours post-dose, the fold difference in the plasma concentrations of the salts of MBX-2982 when compared to the micronized, free-base form of 2982 are 94 fold higher plasma concentration (HCl form I), 186 fold higher plasma concentration (HCl form II), 7 fold higher plasma concentration (mesylate), and 40 fold higher plasma concentration (tosylate).

Modifications to the invention will be apparent to one of skill in the art given this disclosure. Such modifications and the resulting equivalents to the embodiments and examples described above are intended to be included within the scope of the following claims.

What is claimed is:

1. A crystalline salt of 5-ethyl-2-{4-[4-(4-tetrazol-1-yl-phenoxymethyl)-thiazol-2-yl]-piperidin-1-yl}-pyrimidine selected from the group consisting of:
   besylate salt, which has substantially the same X-ray power diffraction (XRPD) pattern as shown in FIG. 15;
   camsylate salt, which has substantially the same X-ray power diffraction (XRPD) pattern as shown in FIG. 16;
   esylate salt, which has substantially the same X-ray power diffraction (XRPD) pattern as shown in FIG. 17;
   HBr salt, which has substantially the same X-ray power diffraction (XRPD) pattern as shown in FIG. 18;
   sulfate salt, which has substantially the same X-ray power diffraction (XRPD) pattern as shown in FIG. 20;
   tosylate salt, which has substantially the same X-ray power diffraction (XRPD) pattern as shown in FIG. 21; and
   HCl salt, which has substantially the same X-ray power diffraction (XRPD) pattern as shown in FIG. 22.

2. A crystalline HCl salt of 5-ethyl-2-{4-[4-(4-tetrazol-1-yl-phenoxymethyl)-thiazol-2-yl]-piperidin-1-yl}-pyrimidine having substantially the same XRPD pattern as shown in FIG. 22.

3. A crystalline HCl salt of 5-ethyl-2-{4-[4-(4-tetrazol-1-yl-phenoxymethyl)-thiazol-2-yl]-piperidin-1-yl}-pyrimidine that is a polymorph (Form I) having a XRPD pattern comprising peaks at degrees 2-theta diffraction angles of about 8.8, 10.8, 16.1, 17.4, 20.4, 20.9, 21.5, 21.7, 26.6, and 28.1.

4. The polymorph of claim 3 having substantially the same XRPD pattern as shown in FIG. 1.

5. The polymorph of claim 3 having a DSC thermogram comprising an endotherm onset at about 191° C.

6. The polymorph of claim 3 having a DSC thermogram substantially as shown in FIG. 2.

7. The polymorph of claim 3 having a Raman spectrum substantially as shown in FIG. 4.

8. A crystalline HCl salt of 5-ethyl-2-{4-[4-(4-tetrazol-1-yl-phenoxymethyl)-thiazol-2-yl]-piperidin-1-yl}-pyrimidine that is a polymorph (Form II) having a XRPD pattern comprising peaks at degrees 2-theta diffraction angles of about 7.8, 10.1, 12.5, 18.4, 19.0, 20.8, 23.0, and 23.5.

9. The polymorph of claim 8 having substantially the same XRPD pattern as shown in FIG. 5.

10. The polymorph of claim 8 having a DSC thermogram comprising an endotherm onset at about 150° C.

11. The polymorph of claim 8 having a DSC thermogram substantially as shown in FIG. 6.

12. A pharmaceutical composition comprising the crystalline salt of claim 1.

* * * * *